(12) United States Patent
Herekar et al.

(10) Patent No.: US 8,945,101 B2
(45) Date of Patent: Feb. 3, 2015

(54) METHOD AND APPARATUS FOR TREATMENT OF OCULAR TISSUE USING COMBINE MODALITIES

(75) Inventors: Satish V. Herekar, Palo Alto, CA (US); Edward E. Manche, Los Altos, CA (US); Donald J. Eaton, Los Altos, CA (US)

(73) Assignee: Seros Medical, LLC, Los Altos, CA (US)

( * ) Notice: Subject to any disclaimer, the term of this patent is extended or adjusted under 35 U.S.C. 154(b) by 504 days.

(21) Appl. No.: 13/068,126

(22) Filed: May 2, 2011

(65) Prior Publication Data
US 2011/0282333 A1 Nov. 17, 2011

Related U.S. Application Data

(63) Continuation of application No. 61/330,168, filed on Apr. 30, 2010.

(51) Int. Cl.
*A61B 18/20* (2006.01)
*A61N 5/067* (2006.01)
(Continued)

(52) U.S. Cl.
CPC ............ *A61N 5/062* (2013.01); *A61F 9/00821* (2013.01); *A61F 9/0079* (2013.01); *A61F 2009/00851* (2013.01);
(Continued)

(58) Field of Classification Search
USPC .......... 606/4–6, 10–12, 166, 167; 607/88, 89, 607/96, 100; 128/898
See application file for complete search history.

(56) References Cited

U.S. PATENT DOCUMENTS 5,779,696 A * 7/1998 Berry et al. ............... 606/16
6,099,521 A * 8/2000 Shadduck ............... 606/4
(Continued)

FOREIGN PATENT DOCUMENTS

AU 2004 200303 2/2004
AU 2007202052 5/2007
(Continued)

OTHER PUBLICATIONS

Gevorkian et al., "Thermal (In)Stability of Type 1 Collagen Fibrils", The Am. Phys. Soc. 102, 4 pgs (2009).
(Continued)

*Primary Examiner* — Ahmed Farah
(74) *Attorney, Agent, or Firm* — Squire Patton Boggs (US) LLP

(57) ABSTRACT

An apparatus and a method are provided for treating a targeted area of ocular tissue in a tissue-sparing manner comprising use of two or more therapeutic modalities, including thermal radiation source (such as an CW infrared fiber laser), operative in a wavelength range that has a high absorption in water, and photochemical collagen cross-linking (CXL), together with one or more specific system improvements, such as peri-operative feedback measurements for tailoring of the therapeutic modalities, an ocular tissue surface thermal control/cooling mechanism and a source of deuterated water/riboflavin solution in a delivery system targeting ocular tissue in the presence of the ultraviolet radiation. Additional methods of rapid cross-linking (RXL), are provided that further enables cross-linking (CXL) therapy to be combined with thermal therapy.

10 Claims, 18 Drawing Sheets

(51) Int. Cl.
*A61F 7/00* (2006.01)
*A61N 5/06* (2006.01)
*A61F 9/008* (2006.01)
*A61F 9/007* (2006.01)

(52) U.S. Cl.
CPC ............ *A61F 2009/00853* (2013.01); *A61F 2009/00872* (2013.01); *A61N 2005/0659* (2013.01)
USPC ......... 606/4; 606/3; 607/89; 607/96; 607/100

(56) References Cited

U.S. PATENT DOCUMENTS

| | | |
|---|---|---|
| 6,334,856 B1 | 1/2002 | Allen |
| 6,503,231 B1 | 1/2003 | Prausnitz et al. |
| 6,611,707 B1 | 8/2003 | Prausnitz et al. |
| 6,743,211 B1 | 6/2004 | Prausnitz et al. |
| 7,226,439 B2 | 6/2007 | Prausnitz et al. |
| 7,344,499 B1 | 3/2008 | Prausnitz et al. |
| 7,918,814 B2 | 4/2011 | Prausnitz et al. |
| 8,545,487 B2 * | 10/2013 | Muller et al. .......... 606/5 |
| 2002/0082543 A1 | 6/2002 | Park |
| 2004/0093046 A1 * | 5/2004 | Sand .................. 607/89 |
| 2005/0137531 A1 | 6/2005 | Prausnitz |
| 2007/0083190 A1 * | 4/2007 | Domankevitz .......... 606/9 |
| 2007/0123845 A1 * | 5/2007 | Lubatschowski ........ 606/5 |
| 2007/0225676 A1 | 9/2007 | Prausnitz |
| 2008/0015660 A1 * | 1/2008 | Herekar .............. 607/88 |
| 2008/0039769 A1 | 2/2008 | Peyman |
| 2009/0149923 A1 * | 6/2009 | Herekar .............. 607/88 |
| 2009/0182306 A1 | 7/2009 | Lee |
| 2010/0114109 A1 * | 5/2010 | Peyman ............. 606/107 |
| 2010/0210996 A1 * | 8/2010 | Peyman .............. 604/20 |
| 2010/0256597 A1 | 10/2010 | Prausnitz |
| 2010/0312191 A1 | 12/2010 | Allen |
| 2013/0023966 A1 * | 1/2013 | Depfenhart et al. ........ 607/89 |

FOREIGN PATENT DOCUMENTS

| | | |
|---|---|---|
| CA | 2330207 | 12/1999 |
| CA | 2510389 | 12/1999 |
| CA | 2376128 | 12/2000 |
| EP | 1086214 | 3/2001 |
| JP | 2009-055747 | 3/2009 |
| WO | WO 90/12618 | 11/1990 |
| WO | WO 2007/131050 | 11/2007 |
| WO | WO 2009/094394 | 7/2009 |

OTHER PUBLICATIONS

Vangsness et al., "Collagen Shortening", Clinical Orthopaedics and Related Research, pp. 267-271 (1997).
European Search Report EP 11775711, mailed Oct. 7, 2013, 9 pgs.

* cited by examiner

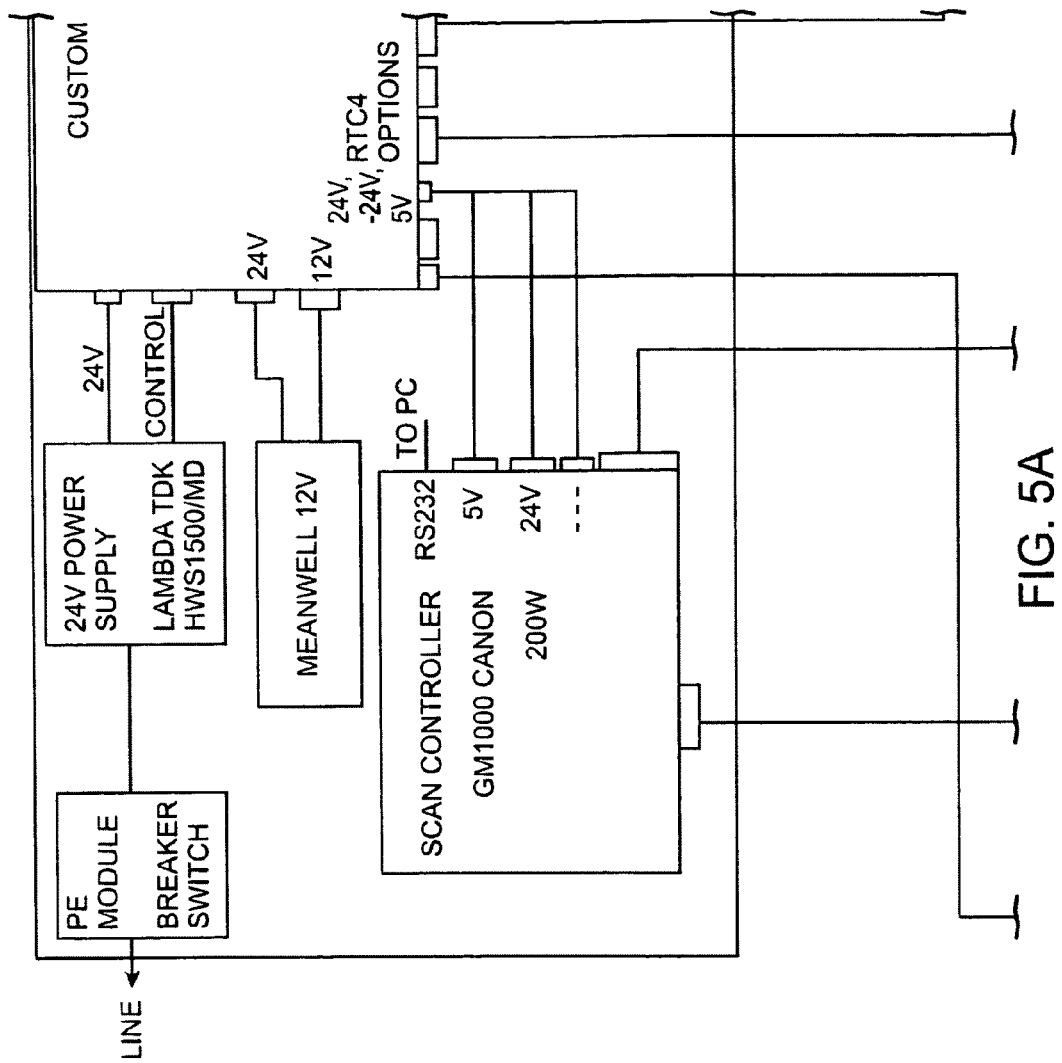

METHOD AND APPARATUS FOR TREATMENT OF OCULAR TISSUE USING COMBINE MODALITIES

CROSS-REFERENCE TO RELATED APPLICATION

This application claims benefit of and incorporates by reference U.S. Patent Application No. 61/330,168 which was filed on Apr. 30, 2010.

BACKGROUND OF THE INVENTION

This invention relates to apparatus and methods for treatment of ocular tissue and more particularly to altering opto-mechanical characteristics of targeted ocular tissue with the use of a continuous wave (CW) infrared laser in combination with other treatment modalities. This invention includes both the precise reshaping of corneal tissue for refractive correction and novel techniques for cross-linking the thermally treated corneal tissue to prevent such tissue from regressing to its original shape.

Overview of Current Cross-Linking Technology

Cross-linking is a widespread method used to harden polymer materials and to stabilize living tissue. More specifically in the medical arena, collagen cross-linking (CXL) and bonding technology has been used for many years in dentistry, orthopedics, and dermatology.

In 1998, a breakthrough occurred in ophthalmology when Theo Seiler, MD, PhD, of Zurich, Switzerland, used CXL to treat severe keratoconus (a progressive degenerative condition of the cornea where the tissue thins and bulges forward). By 2000, after significant research into the safety aspects of this procedure by Dr. Seiler, Gregor Wollensak, MD, and Eberhard Spoerl, PhD (Germany), CXL was adopted by surgeons worldwide outside of the U.S. (In the US, clinical trials for the current version of CXL are underway.) In 2007 CXL received regulatory approval as a procedure in the European Union.

The primary emphasis in the application of CXL for ophthalmology has been in the treatment of keratoconus, which is prevalent in about one in 2,000 people in the United States. This condition is manifested by a weak cornea that becomes too elastic and stretches, causing it to bulge outward. This condition changes the curvature of the cornea, which almost always leads to poor visual acuity (not correctable with glasses and/or soft contact lenses) that requires the use of rigid gas permeable lenses. Thus, when the cornea begins losing its shape (i.e., becomes cone shaped instead of spherical), nearsightedness (myopia) and irregular astigmatism result, which causes the blu'rring of vision. As this condition progresses, scarring and a very irregular corneal curvature may result. If a person cannot be helped with rigid contact lenses, then a corneal transplantation can be required.

There are other conditions/corneal diseases where the cornea can become stretched and distorted, for example, such as surgically induced astigmatism. Another of these, where CXL is currently being utilized for correction, is in corneal ectasia. This condition involves stretching of the cornea (a collagen tissue) that occurs after refractive surgeries, such as laser in situ keratomileusis (LASIK) or photo-refractive keratectomy (PRK). Other corneal diseases in which CXL treatment has been tried successfully include corneal ulceration (possible sequelae to bacterial, viral or fungal infections) and bullous keratopathy (excess fluid accumulation causing corneal edema).

The biomechanical basis of increased corneal strength (i.e., stability and stiffness) is the result of the formation of covalent cross-links that occur when the photosensitizer, riboflavin (Vitamin B-2), is applied to the de-epithelialized surface of the cornea. This excitation of the riboflavin by the UVA results in the creation of free radicals that interact with amino acids in neighboring collagen molecules to form strong chemical bonds.

Known CXL procedures are effective, but they are invasive and time-consuming, and they may have potential safety issues. In known procedures, 0.1% riboflavin is formulated with a polysaccharide made of many glucose molecules such as dextran, and then the surface layer of the cornea (epithelium) is surgically removed so the riboflavin can pass (i.e., be absorbed) into the stroma (collagen layers) of the cornea. The riboflavin is applied with an eye dropper manually every 3 to 5 minutes for a total of 30 minutes prior to treatment (the pre-soak procedure). Following the pre-soak a continuous UVA light (wavelength of approximately 365-370 nm) is projected on the cornea for approximately 30 minutes, and there is no mechanism for measuring the depth of irradiation. During UVA irradiation riboflavin is continuously applied manually every 3 to 5 minutes with an eye dropper.

Limitations of Existing CXL

In known procedures, there is no measurement as to how much riboflavin is in the stroma during the treatment, and there is no means to assure prevention of cell damage in the corneal endothelium, or in the limbus, which contains vital corneal limbal stem cells.

In short, the existing procedure employing CXL has been clinically proven (in Europe) to be safe. However, in its current form, the procedure is very crude and exhibits a number of significant limitations including but not limited to the following: the procedure takes too long (approximately one hour in total); removal of the corneal epithelium is required, making the procedure invasive and uncomfortable for the patient intra-operatively and for 3 to 4 days following surgery. These limitations clearly preclude the use of CXL for many corneal treatments that would require a fast and highly accurate process for stiffening and stabilizing the cornea.

Overview of Corneal Thermal Reshaping

It is known that thermal treatment of the cornea with various laser devices can reshape the cornea for refractive correction. Although some of the known thermal treatments have been FDA approved in the USA, all have eventually failed because of the natural regression of the cornea to its original shape. This regression may occur over time periods of months to a few years. Companies known to have been active in the field are Refractec (Conductive Kerotoplasty—CK), Thermal Vision, aka Avedro (Keraflex), Rodenstock (Diode Thermal Kerotoplasty—DTK withdrawn) and Sunrise (Laser Thermal Kerotoplasty—LTK withdrawn). However, there remains a need to predictably re-shape and stabilize the cornea after the thermal treatment, to increase the long-term success rate.

None of the aforementioned thermal treatments have been surface sparing, which means the outer layers of the cornea (epithelium and Bowman's membrane) may be damaged by these treatments. There are a number of negative outcomes that can occur from such damage: (1) there is pain and wound healing that can induce corneal haze and leave the cornea vulnerable to infection; (2) the structural integrity of the cornea is negatively impacted; (3) near-term predictability of refractive outcomes is poor. These negative outcomes can be alleviated by a thermal procedure which spares the epithelium and Bowman's membrane. The delivery of thermal radiation in a surface-sparing fashion has been performed in dermatology applications for surface treatment. These applications involve heat transfer that occurs as a result of passing thermal radiation through a cooled custom contact window on the skin, thereby protecting the epidermal layer.

SUMMARY OF THE INVENTION

Embodiments of the present invention comprise combined treatment modalities that include an apparatus and a method for providing treatment to targeted areas of ocular tissue. These embodiments of the invention comprise the use of two or more therapeutic modalities, including a thermal radiation source (such as a CW infrared laser), operative in a wavelength range that has a high absorption in water, and can be delivered with a surface heat extraction mechanism; temperature or thermal control mechanism; or cooling mechanism (such as an ocular tissue surface thermal control/cooling device, e.g., with a sapphire lens). The thermal treatment modality is combined with photochemical collagen cross-linking, together with one or more optional specific system improvements, such as feedback measurements using optical coherence tomography (OCT), monitoring, amongst others, for tailoring of therapeutic modalities. Another therapeutic modality is a collagen cross-linking promoting agent, in particular, a formulation of deuterated water and riboflavin solution (plus other possible excipients) in a delivery system targeting ocular tissue in the presence of the ultraviolet radiation. New methods of more rapid cross-linking than what occurs with existing CXL, and, in its non-invasive embodiment are provided. When the rapid cross-linking (herein "RXL") is combined with the thermal subsurface (herein "TS") technology described herein, this combination is defined as TS-RXL.

According to this TS-RXL process, a thermal control/heat exchanging/cooling modality is applied to the surface of the eye while injecting infrared radiation to invoke intra-stromal thermal effects (i.e., shrinkage) that promote corneal reshaping accompanied by rapid cross-linking. The thermal control/cooling mechanism may be a target-surface-mountable lens of highly thermally conductive material, such as sapphire, that is juxtaposed to the ocular tissue. Methods operative in accordance with the invention produce intended subsurface lesions that reshape ocular tissue resulting in a stable form, because this thermal reshaping is followed by the application of RXL, which prevents regression thereof.

The invention will be better understood by reference to the following detailed description in connection with the accompanying drawings.

DETAILED DESCRIPTION OF THE INVENTION

Figure 1:
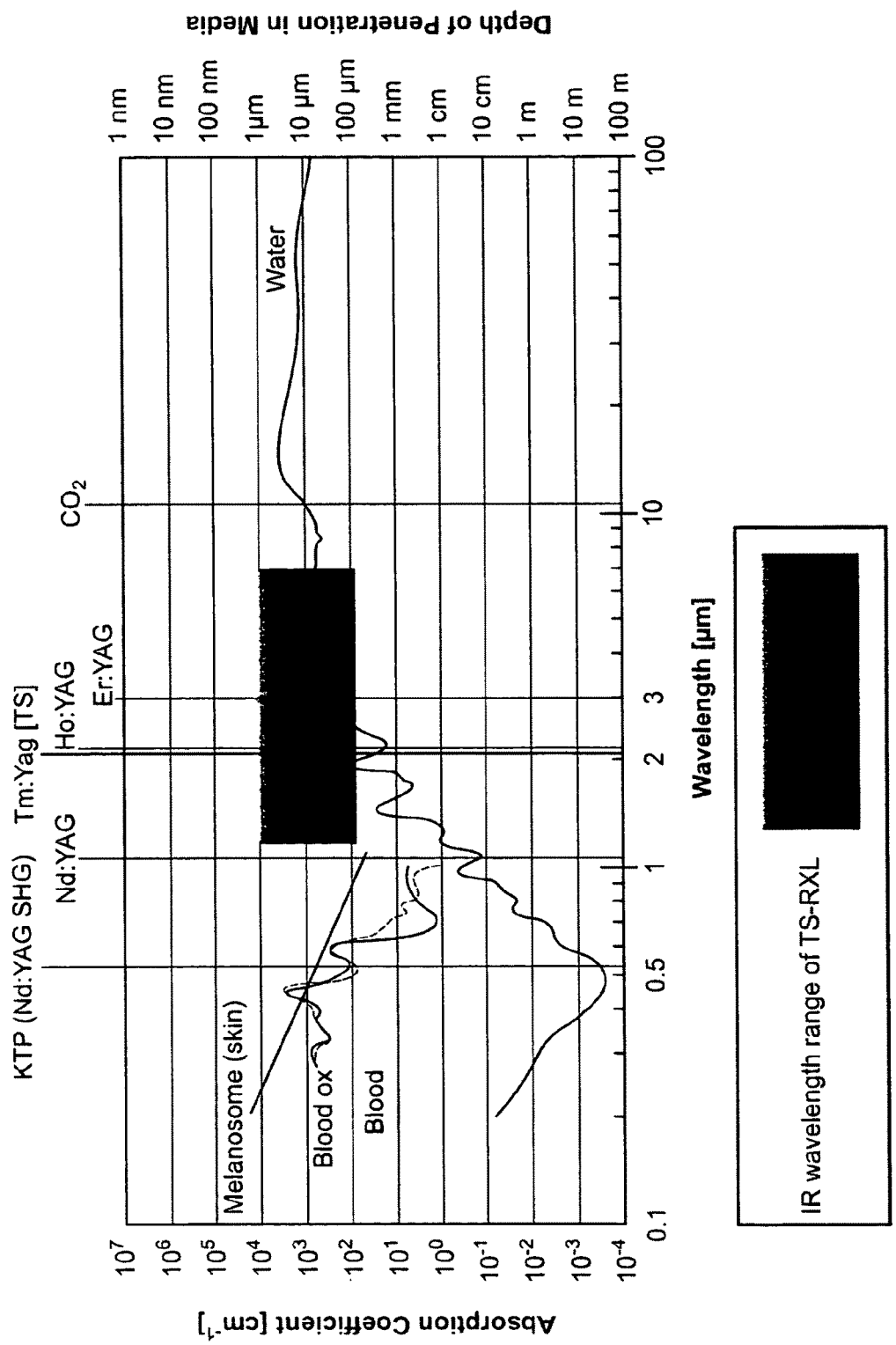
FIG. 1 is a spectral graph showing absorption parameters and range of wavelengths that could be used according to the invention.

The invention includes a method and apparatus for treatment of ocular tissue that spares the outer layers (epithelium and Bowman's membrane) of the cornea during the application of combined therapeutic modalities. The combined therapeutic modalities include subsurface thermal remodeling and rapid collagen cross-linking (TS-RXL). The first therapeutic modality, thermal remodeling, pertains to the altering of the shape of targeted ocular tissue with the use of thermal energy, preferably in the form of a programmable XY-scanning continuous wave (CW) infrared fiber laser. This laser is operated at a wavelength range that has a high absorption in water (penetration depth of 0.1 mm to 1 mm, 0.2 mm to 0.6, or 0.4 to 0.5 mm, for example, 0.5 mm penetration depth typically, see FIG. 1) thereby also protecting the endothelium. The second therapeutic modality involves the peri-operative (which is herein defined as pre-, intra-, and/or post-the application of thermal radiation) cross-linking of collagen tissue to enhance stiffness, shape and/or stability of the treated tissue, that may be effected through a photochemical process utilizing UVA and riboflavin.

As a key feature of the invention, the thermal and photochemical energy and dosing is subject to programmable customization based on integrated feedback and control from peri-operative measuring systems such as, topographic, wavefront, and/or optical coherence tomography (OCT) measurement. Both thermal and UVA therapeutic modalities can be further augmented by employing these various measurements for customized treatments. Such measurements may provide feedback to more precisely tailor the therapeutic modalities for a particular condition or a specific patient need. For example, topographic, fluorescent (including auto-fluorescence) and/or OCT measurements may be used to tailor the dosing, temperature, location, intensity, duration, or energy patterns of the two therapeutic modalities.

In addition to the combination of thermal and photochemical therapeutic modalities with feedback control, the invention encompasses one or more fundamental and enabling improvements that will provide a gentleness (such as minimal opacification) of treatment. For example: 1) surface cooling/thermal control of the cornea associated with thermal treatment, which enables epithelium-sparing thermal treatment; 2) a combination of controlled power and scanning speed of the thermal laser beam for customization of treatment; and, 3) real-time OCT guided thermal delivery. It is significant and surprising that cross-linking becomes more effective because of the surface (which includes both epithelium and Bowman's membrane) cooling/thermal control/sparing application (See FIG. 9). Peri-operative control information is provided for both the thermal procedure and rapid cross-linking (as described herein). The end result of these combined modalities is to provide highly accurate thermal corneal reshaping, together with enduring stability of outcomes; plus, this procedure is performed in a minimally invasive manner.

Rapid cross-linking (RXL) is herein defined as an effective (increasing stiffness by at least 50%) level of collagen cross-linking in less than 5 to 15 minutes. Several techniques can contribute to more rapid cross-linking. One method of RXL comprises, in a further combination, the more rapid stabilization of corneal tissue by means of application of pulsed, fractionated ultraviolet radiation (as such feature is described in U.S. patent application Ser. No. 12/273,444 published as US-2009-0149923-A1, which is hereby incorporated by reference herein in its entirety) in the presence of the application of a deuterated water solution of riboflavin to the corneal surface (as such feature is described in WO 2011/019940, which is hereby incorporated by reference herein in its entirety), the combination of which is an effective embodiment of RXL.

Thermal Therapeutic Modality and Delivery

Figure 6:
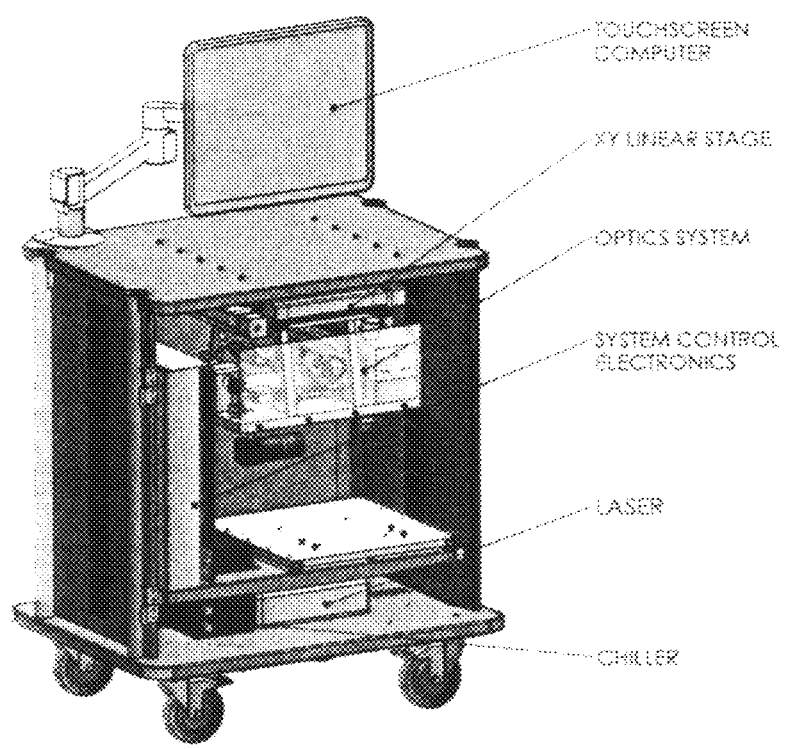
FIG. 6 is a composite drawing of an entire exemplar apparatus suitable for practicing the invention, detailing key components.
Figure 8:
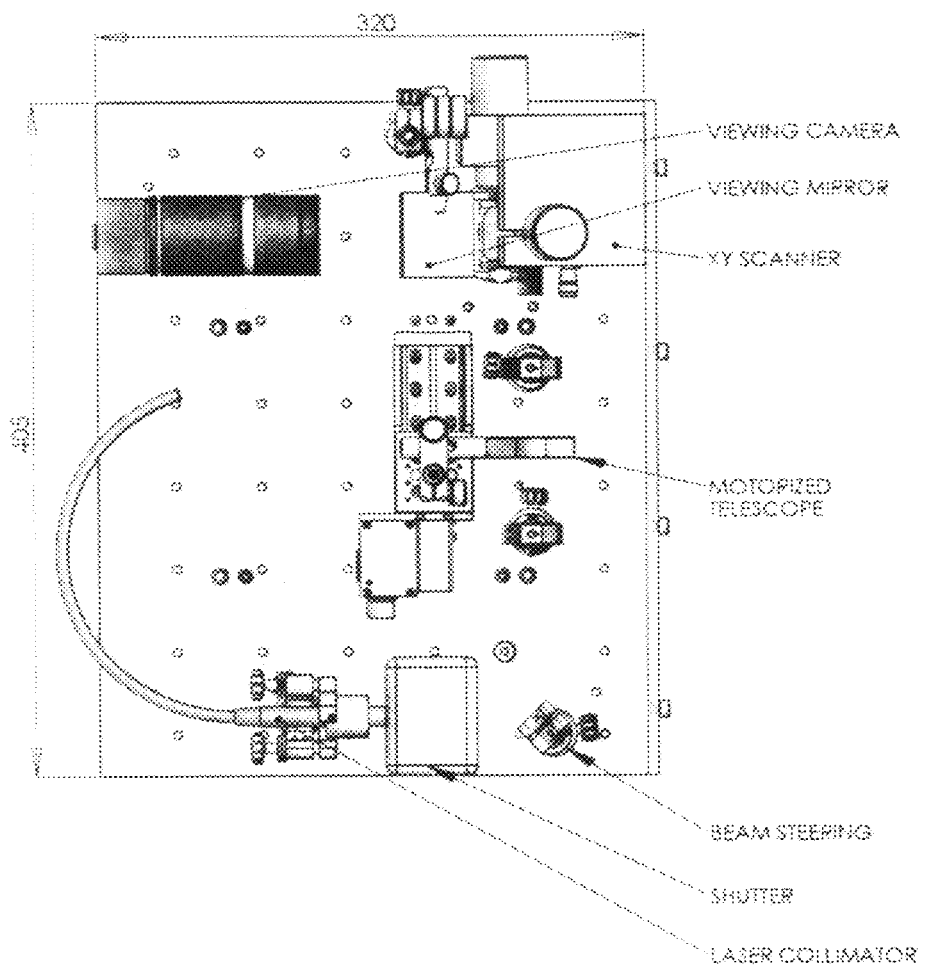
FIG. 8 is a top view of the following system optics: telescope for magnification adjust, XY scanner, Collimator, Eye viewing and pupil monitoring camera.
Figure 10:
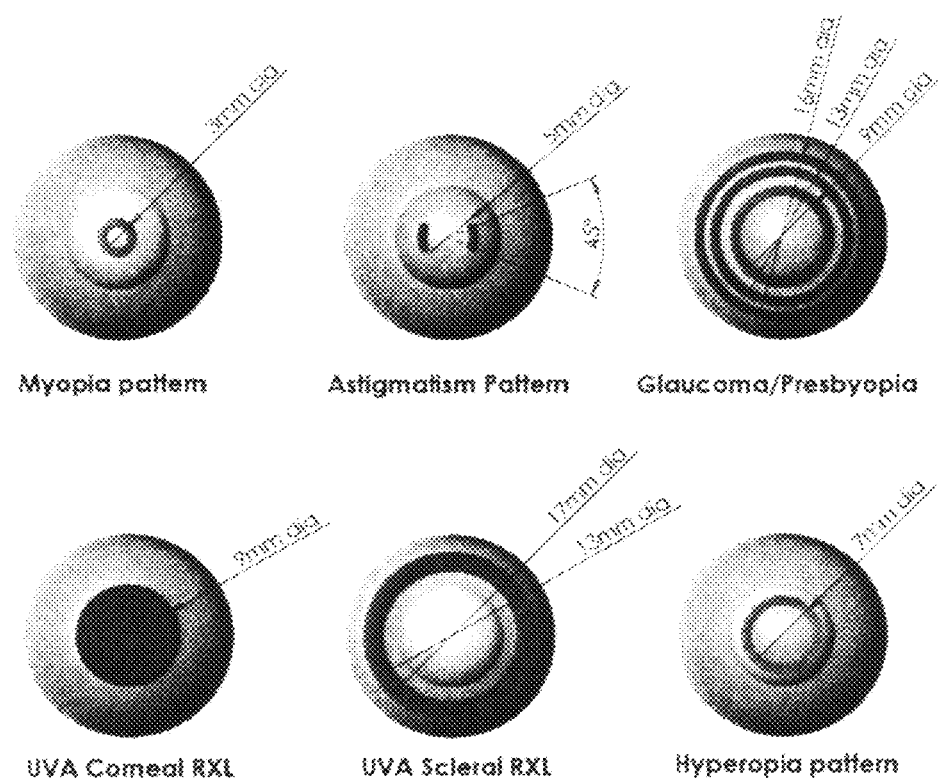
FIG. 10 shows exemplary thermal patterns that may be delivered for various treatment conditions, which may be further individualized according to the specific characteristics of the treated patient, as well as through feedback, as described herein.

In the thermal radiation technique, a preferred embodiment is shown in the exemplar apparatus of FIG. 6, where a CW infrared fiber laser beam is the source of thermal radiation, and is delivered to the ocular tissue via a fiber coupled XY scanner that projects pre-selected patterns for delivering said thermal radiation onto ocular tissue. The XY scanner of the exemplar apparatus is shown in FIG. 8. A key benefit of the XY scanner is to significantly increase the flexibility for customizing thermal energy patterns for a variety of ocular conditions. Such a scanner permits the inclusion of highly integrated (speed+power+position+depth) and precise patterns that are designed and programmed to treat a variety of ocular conditions (myopia, astigmatism, glaucoma, presbyopia, hyperopia, keractoconus and ectasia). These patterns may be pre-programmed or adjusted during a given treatment procedure by the surgeon and/or through the use of feedback mechanisms, as will be detailed below. FIG. 10 illustrates examples of such patterns. In addition, flexibility is built into the apparatus to permit the surgeon the option to intervene and redirect the apparatus to generate new or patient-personalized pattern selections. This personalization capability illustrates the advantages and efficacy of the treatment.

Figure 7:
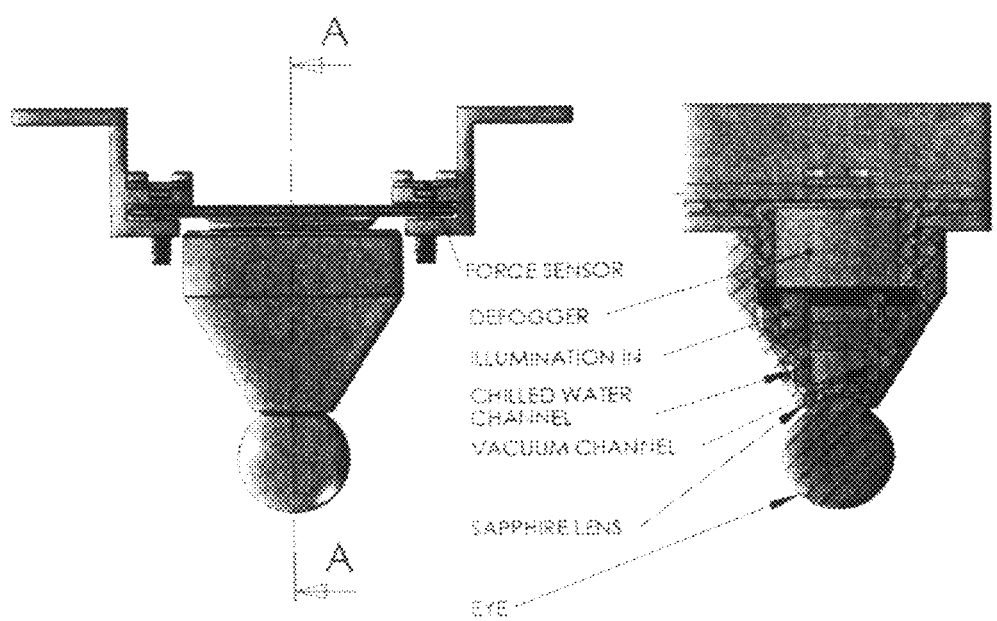
FIG. 7 depicts side and cross-sectional views of a patient interface assembly cone that houses components for corneal applanation.
Figure 13:
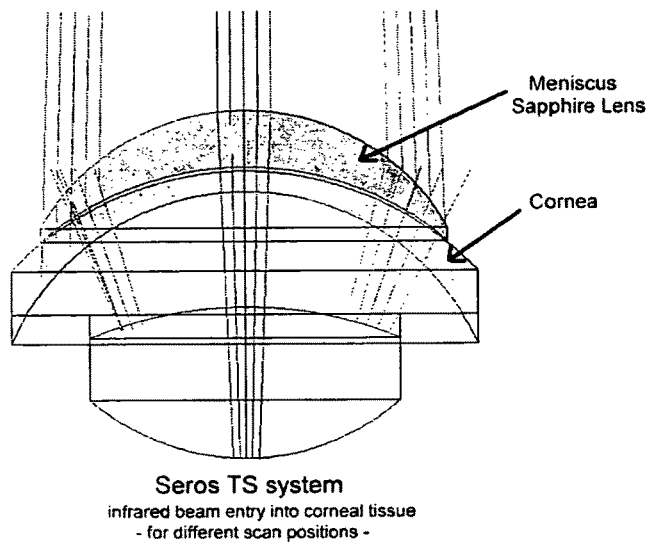
FIG. 13 shows ray-tracing simulation at the sapphire meniscus lens-eye interface

The thermal radiation in the exemplar apparatus of this method is delivered with adjustable scan speed and laser power through a temperature controlled/chilled custom applanation lens. This lens may be made of a material such as sapphire, diamond coated glass, or clear YAG that provides high thermal conductivity, high heat capacity and optical transmission or by other means for thermal control/cooling the surface, such as a cryospray. This thermal control/cooling results in low collagen impact/disruption in the corneal stroma, and produces only a moderate sub-surface thermal temperature increase (i.e., less than about 85 deg C.). The result of this thermal control/cooling also provides protection to the epithelium and Bowman's layers of the cornea from the thermal application. Illustrations of the thermal cone features of the examplar apparatus are depicted in FIG. 7 and FIG. 13. FIG. 7 depicts side and cross-sectional views of a patient interface assembly cone that houses components for corneal applanation temperature. FIG. 7 shows a sapphire lens which is a thermal laser window as well as OCT light delivery window, water channel for cooling water that is used to control the temperature of the sapphire lens, a lens defogger (pumped air nozzle) for defogging the sapphire lens, a suction ring labeled as vacuum channel, illuminator in for camera illumination, and a force sensor to sense force applied by the cone to the eye in excess of that by the suction ring.

The exemplar apparatus uses a thermal radiation source, such as a CW infrared fiber laser, which has a wavelength in the range of 2013 nm (Tm:YAG). However, this apparatus may in the future be changed or upgraded whereby the CW infrared fiber laser may offer a tunable wavelength. This type of tunable CW fiber laser will enable a wavelength selection between 1.4 µm to 1.54 µm or 1.86 um to 2.52 µm. These optical wavelengths provide an absorption length in water in the range of 200 µm to 600 µm, which is appropriate for the intended application and may provide such a range of penetration depth in ocular tissue. FIG. 1 shows absorption parameters and range of wavelengths that could be used. Other lasers could be included in this system which may have one or more fixed wavelengths or may be tunable. These laser features are presently embodied in the solid state lasers using the aforementioned Tm:YAG laser crystal, or such laser features can also be obtained using Tm fiber lasers or semiconductor lasers with electrical or optical excitation. The primary purpose of having this wavelength selection feature is to vary the penetration depth of the laser beam.

Those skilled in the art will note that other methods of thermal radiation are available and known in the field, encompassing other laser, microwave, radio-frequency (RF), electrical and ultrasound energy sources, and the invention is not here intended to be limited to the aforementioned CW infrared fiber laser.

Key Design Factors for Thermal Delivery

The following are the design factors that distinguish the exemplar apparatus' thermal delivery from any prior art, one or more such features being necessary to the practice of the invention:

(1) A cornea-shaped, custom applanation lens (such as Plano-concave or meniscus, approximately 1 mm to 5 mm in thickness & 4 mm to 20 mm in diameter) is fitted on the ocular tissue (See FIG. 13 for illustration and application of lens);

(2) During the entire time or part of the time the thermal radiation source (e.g., a CW infrared fiber laser) is applied, the ocular tissue surface and the stromal collagen tissue are temperature controlled, preferably by a sapphire contact lens. The lens surface may be maintained at a temperature ranging from 0 degrees to 20 degrees C., or from 8 to 18 degrees C. and preferably about 8 to 11 degrees C., during the course of a thermal radiation treatment. Due to the proximity and thermal conductivity of the epithelium and stroma, an effect of the surface thermal control/cooling is to enable the precise control of temperature in the stroma. The surface temperature is continuously monitored and displayed on the PC screen. The invention is not limited to this method of temperature control. Other methods of temperature control may be used, including other methods of direct thermal contact of the tissue surface with heated or cooled solids, liquids, or gases, as well as indirect methods, such as through the use of thermal radiation sources and may be used in the present invention.

(3) A custom suction ring applanates the ocular tissue to the sapphire lens in a gentle manner prior to, throughout, and following the thermal procedure, which enables a precise thermal control/cooling effect on the anterior most membranes to be protected (such as epithelium and Bowman's membranes and conjunctiva or blood vessels). The suction ring also provides greater laser registration and resistance to patient saccadic type movement. (See FIG. 7 for illustration of an exemplar cone with vacuum suction ring assembly.)

Noninvasive Application of Thermal Lesions

Based upon the design factors set forth above, the exemplar apparatus is capable of transmitting thermal radiation through the epithelium and Bowman's membranes (or conjunctiva, during scleral treatment) into the anterior ocular tissue (such as the stroma or sclera), while minimally disrupting these membranes. The result is that, such novel controlled thermal radiation is able to reach collagen fibers beneath these protected membranes, thus sparing the epithelium from adverse effects, such as reduced rates of wound healing, morbidity, scarring and haze formation or susceptibility to infections.

Figure 2:
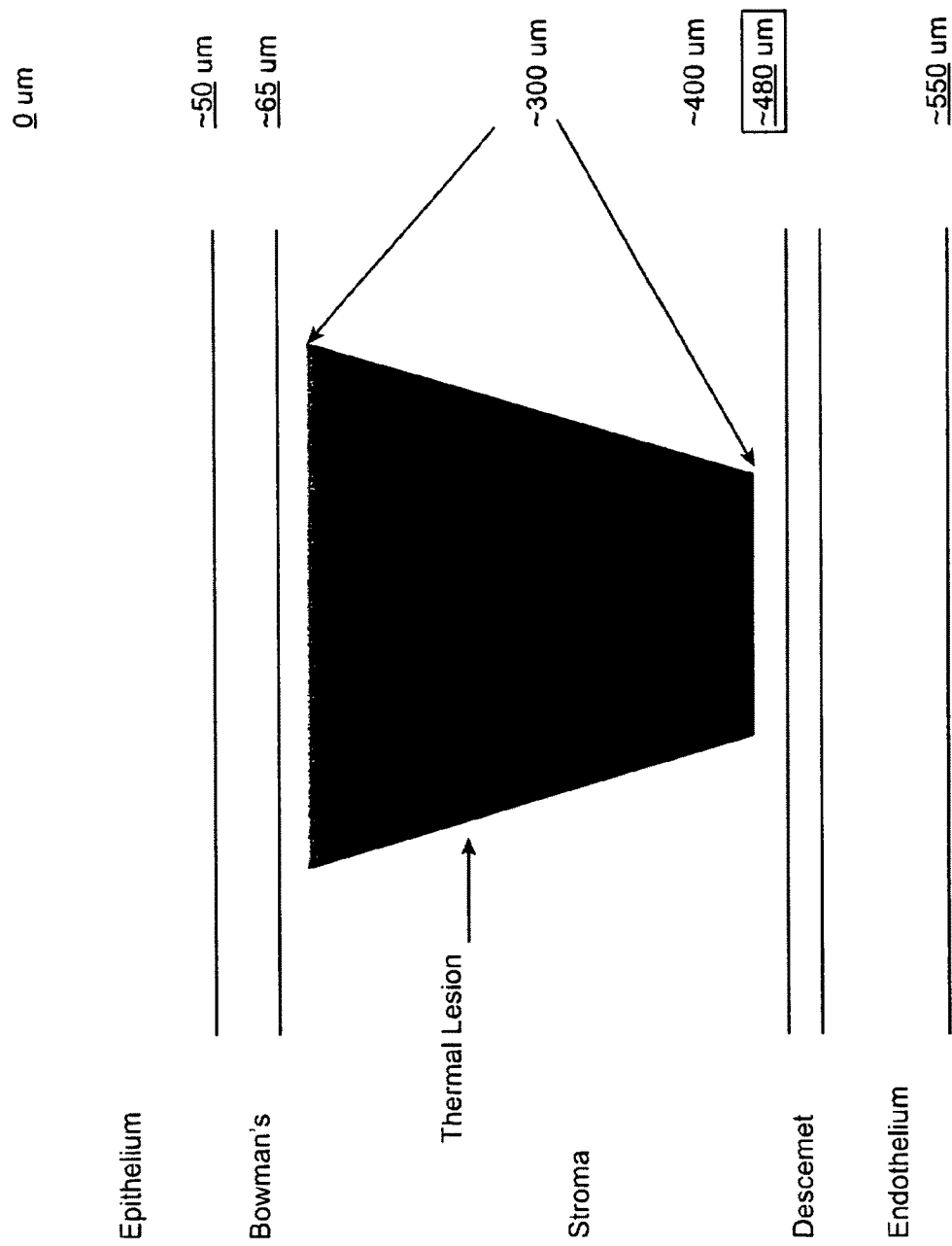
FIG. 2 is a sub-surface lesion schematic diagram illustrating the various layers of the cornea, and a specific region desirable for lesion application and ranges of lesions relative to a surface.

FIG. 2 is a schematic diagram of sub-surface lesions illustrating the various layers of the cornea, and the specific region in the stroma desirable for lesion application and ranges of lesions relative to a surface. See, Vangsness, C, et al., Clinical Orthopaedics and Related Research, Number 337, pp 267-271; Gevorkian, S. G., et al., 102, 048101 (2009), both of which are incorporated by reference herein. The thermal radiation creates a subsurface lesion in the collagen fibers that is preferably controlled to begin approximately 80 μm to 100 μm below the surface. The targeted collagen fibers affected by the lesion begin at this subsurface level and may continue to a typical depth of approximately 300 μm (and preferably within a range of 100 μm to 400 μm). The typical annular lesion created by an annular scan of the thermal radiation may have a width or thickness of the annulus of approximately 0.2 mm to 1 mm. The primary impact of the lesion is controlled at a desired depth and width within the targeted ocular tissue, and will not induce lesions in or adversely affect the Descemet or endothelium membranes.

The precise control of the depth, shape and size of such thermal lesions is a key benefit of the invention. Such precise control is a crucial advantage over previous methods. For the targeted lesion volume, the apparatus is pre-set (via nomograms, Real-Time-OCT, and temperature feedback) to create lesions that provide only controlled limited shrinkage of the collagen fibers.

The system of the invention controls the temperature as a function of depth to induce thermal remodeling or a change in shape of the cornea surface while sparing the surface layers. The temperature is also controlled to obtain the desired remodeling in a short time frame to reduce the treatment time for the patient. The thermal remodeling is induced through thermally induced shrinkage of collagen in the subsurface regions, specifically, the stroma. It is known that collagen shrinkage is induced by thermal treatment (i.e., heating or increase in temperature). The rate of shrinkage or generally time dependence and the manner of modification of collagen are known to depend on the temperature range. Little or no collagen shrinkage is expected to occur below 40 deg C. or 50 deg C. Collagen shrinkage may occur above 50 deg C., however, in the 50 to 60 deg C. range, the shrinkage occurs at a relatively slow rate. In addition, thermally induced collagen shrinkage may be linear up to about 70 to 75 deg C. Above about 75 to 80 deg C. collagen shrinkage is rapid and non-linear, resulting in the unraveling the collagen triple helix.

In the present invention, the temperature of the epithelium and Bowman's layer is preferably controlled to be less than 40 deg C., 40 to 50 deg C., or more narrowly, less than 18 deg C. As a result, no collagen shrinkage is expected or preferred to occur in these regions. However, the temperature in these surface layers can be above 40 deg C. in some embodiments with minimal shrinkage.

In some embodiments, it is preferred to induce local shrinkage in a slow but linear manner for improved near term predictability. Therefore, in the present invention, the stroma is preferably exposed to temperatures of 50 to 75 deg C., or more narrowly, 60 to 65 deg C., 65 to 70 deg C., or 70 to 75 deg C. In such embodiments, it is desirable to control the temperature to be sufficiently low to obtain collagen shrinkage in a linear manner and also controlling the temperature to be sufficiently high to obtain desired thermal remodeling in a short treatment time. However, the invention can further include exposing the stroma to temperatures above 75 or 80 deg C. and can further include inducing shrinkage in a rapid and nonlinear manner. Additionally, the temperature of layers below the stroma, the endothelium and Descemet layers, is controlled so that there is little or no shrinkage, for example, to be less than 50 deg C., or 40 deg C. Furthermore, the creation of lesion boundaries ("edges") can be more accurately defined by using a CW infrared fiber laser beam that is tightly focused. For example, using a laser with a high quality beam which allows for a focal diameter of about 100 μm to about 1 mm at the desired working distance.

Functions of Subsurface Lesions

Figure 3:
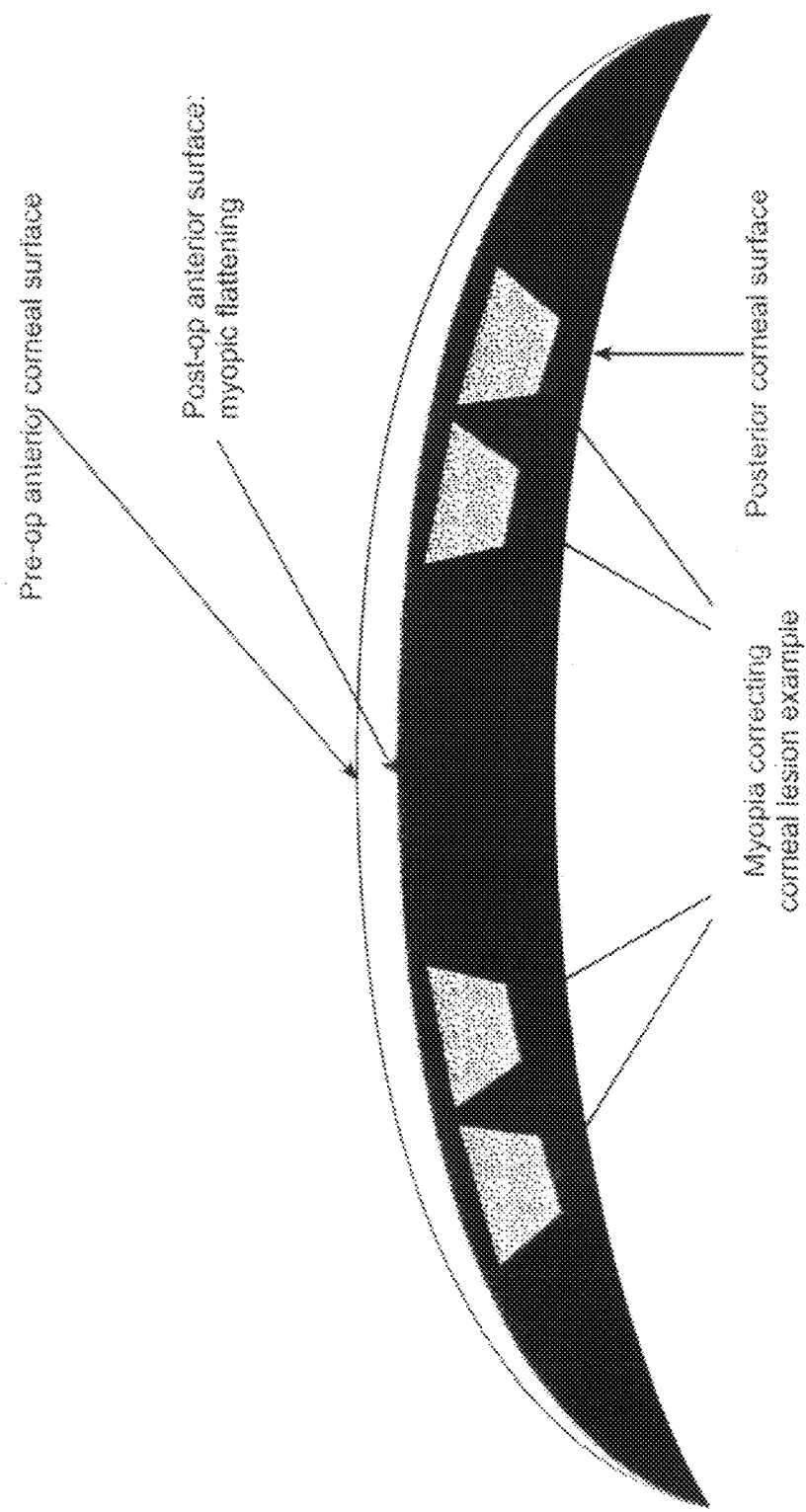
FIG. 3 is a side cross-sectional view of a schematic representation of an exemplary lesion-induced myopic correction.

The sub-surface lesions in the ocular tissue are designed to produce one or a combination of the following effects:

1) The thermal lesions generate collagen shrinkage that cause specific programmed re-shaping of that tissue. Specifically, the reshaping can include flattening or steepening of the cornea corresponding to specific ranges of increase or decrease in diopter, respectively. For example, such re-shaping may flatten (up to or over 5 Diopters) or steepen (up to or over 5 Diopters) the cornea. Additionally, High Order Aberrations (HOA's) may be induced (e.g., by over 2 um). FIG. 3 illustrates an exemplary anterior corneal surface change due to myopic correction showing the corresponding cross-section and lesion location. FIG. 10 illustrates examples of refractive radiation energy treatment patterns for such myopia treatments.

2) The thermal lesions can be applied in sequential patterns which can induce controlled directed tissue translocation (over 1 mm).

3) The thermal lesions can modulate tissue elasticity (i.e., soften ocular tissue by more than 90% of its pre-operative state).

4) The thermal lesions may cause shrinkage of ocular tissue (collagen fibers) that can force the opening of adjacent drainage channels, such as Schlemm's canal and thereby reduce intra-ocular pressure (IOP).

In summary, sub-surface lesions can be produced in ocular tissue that are symmetrically uniform, and thereby distribute stress over a large area of ocular tissue. Such distribution minimizes "hot spots" of biomechanical stress. The foregoing effects of these lesions give versatility to the apparatus thereby enabling it to provide treatments for eye conditions which include, but are not limited to myopia, hyperopia, presbyopia, astigmatism, high order aberrations, and glaucoma.

OCT and Peri-Operative Feedback on Thermal Lesions and Opacity

Figure 4:
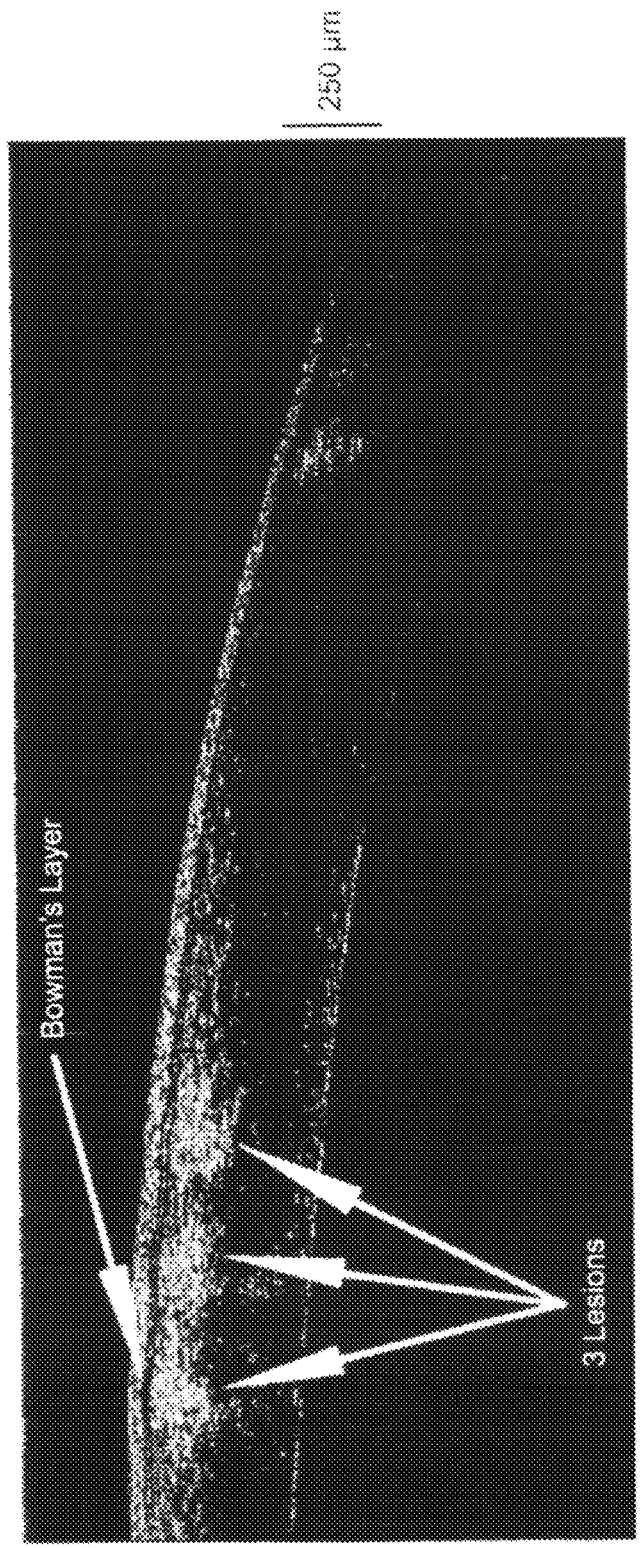
FIG. 4 is a side cross-sectional optical coherence tomography (OCT) image of post thermal sub-surface lesions in a human corneal application.

The exemplar apparatus contains an embedded real-time optical coherence tomography (OCT) engine (such as the ThorLabs Callisto 930 nm) that provides an imaging capability which can scan and display any portion of the cornea in real time (RT). "Real time" refers to the actual time during which a process or event occurs and/or of or relating to a system in which input data is processed within milliseconds or within an acceptable time frame so that it is available virtually immediately as feedback. FIG. 4 shows an OCT image of sub-surface lesions resulting from thermal radiation applied to a human cornea according to the invention. The degree of opacification and depth and size of the lesion at each surface location over which the thermal laser has deposited energy is sampled rapidly by the OCT for extraction of customizing the next exposure pattern of the treatment. The data from such scans can be simultaneously analyzed for the purpose of deriving very precise tissue characteristics. More specifically, this OCT feature provides a special capacity to perform the following:

1) It can generate maps showing the topography and pachymetry (i.e., process of measuring the thickness of the cornea) of the eye's surface both pre-operatively and post-operatively, and in the case of pachymetry measurement, even intra-operatively;

2) It can track the pupil (center) of the eye intra-operatively (in RT) and thereby ascertain proper alignment (centration) of the treatment; the embodiment depicted in FIG. 8 also shows an independent eye pupil center tracking camera.

3) It can monitor intra-operatively the size, depth below surface and degree of opacity of thermal lesions to enhance both the accuracy and safety profile of the treatment.

Additionally, the invention can utilize both external topography and wavefront mapping technologies to assist in treatment planning. This generation and/or utilization of a pre-operative map facilitates the accurate development of a treatment plan to precisely reshape any irregular non-symmetrical condition of the eye. Thermal treatment techniques known in the art, have very limited ability to manipulate the lesion size and/or position of the lesion. Unlike known thermal techniques, the TS system of the invention can create very precisely sized, positioned, and heated volumes of collagen tissue. Further, this is done in a contiguous manner and within reasonable timeframes (for example, between 1-2 minutes in the cornea).

Cone Assembly

Figure 5B:
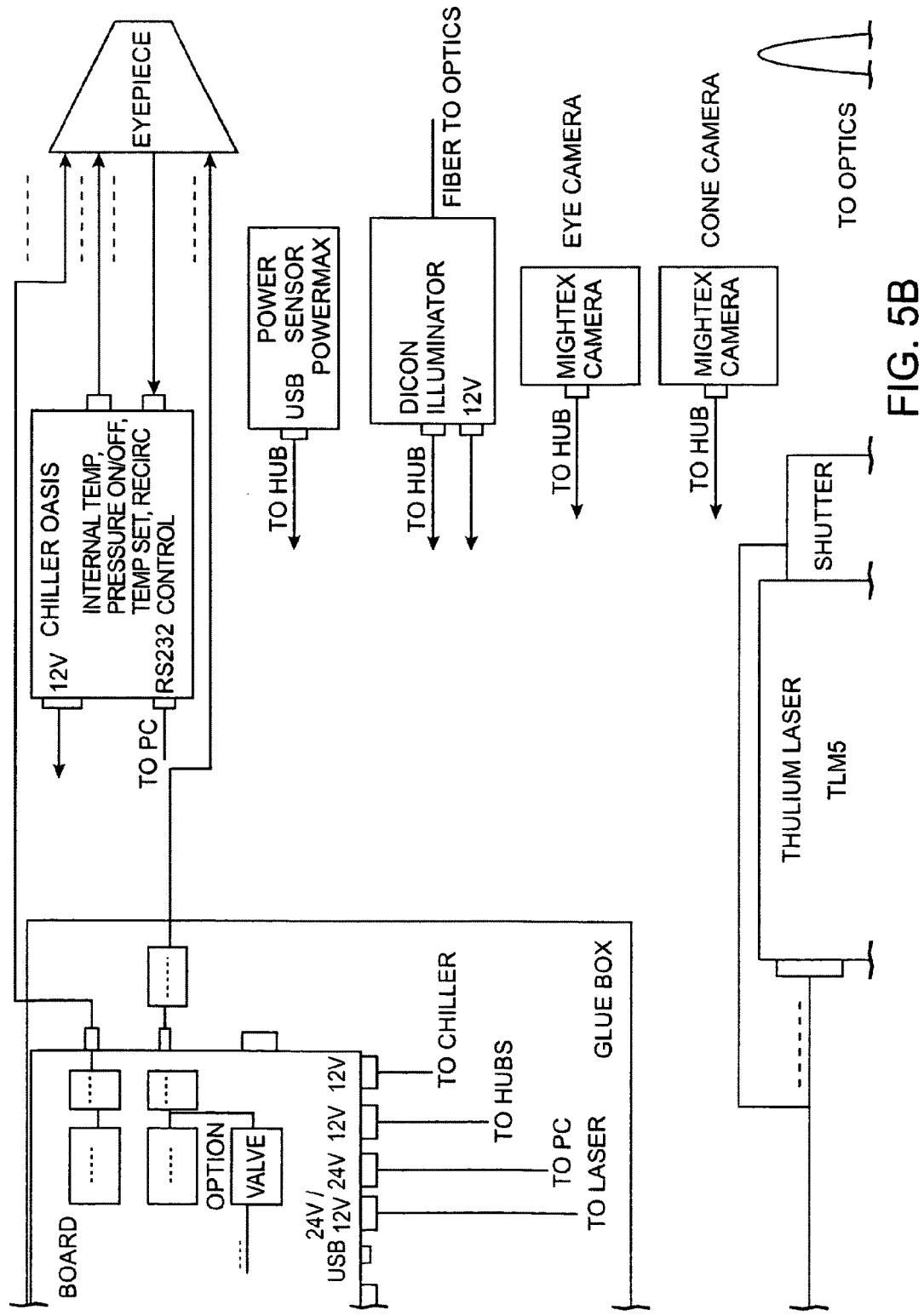
FIG. 5 is a TS system block diagram according to the invention.
Figure 5C:
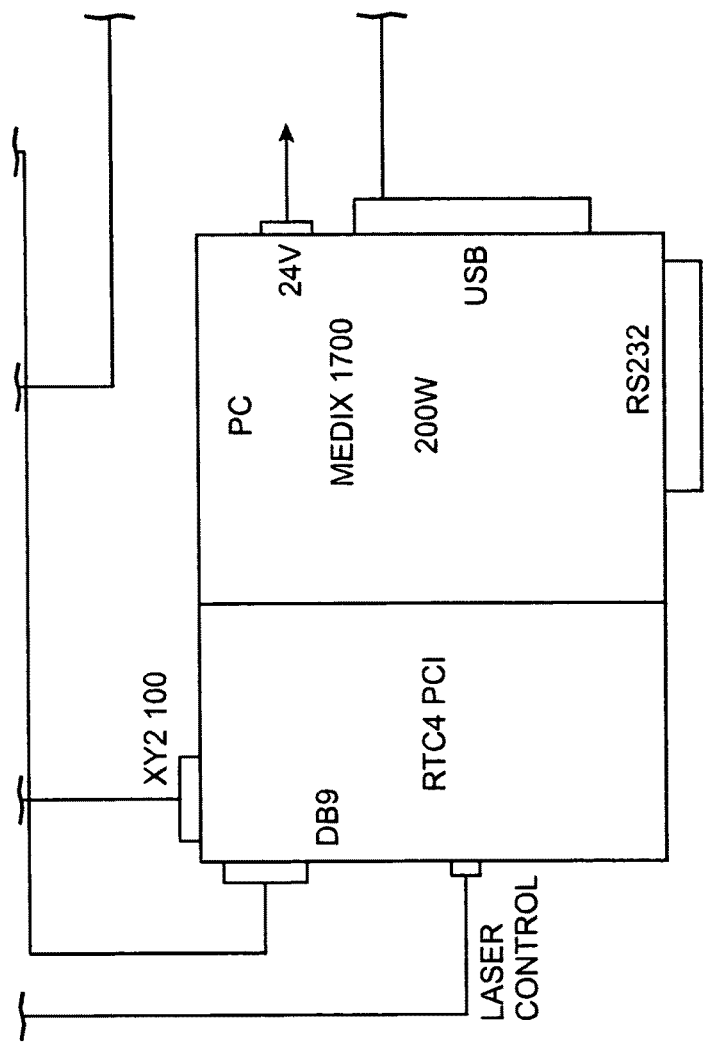
Figure 5D:
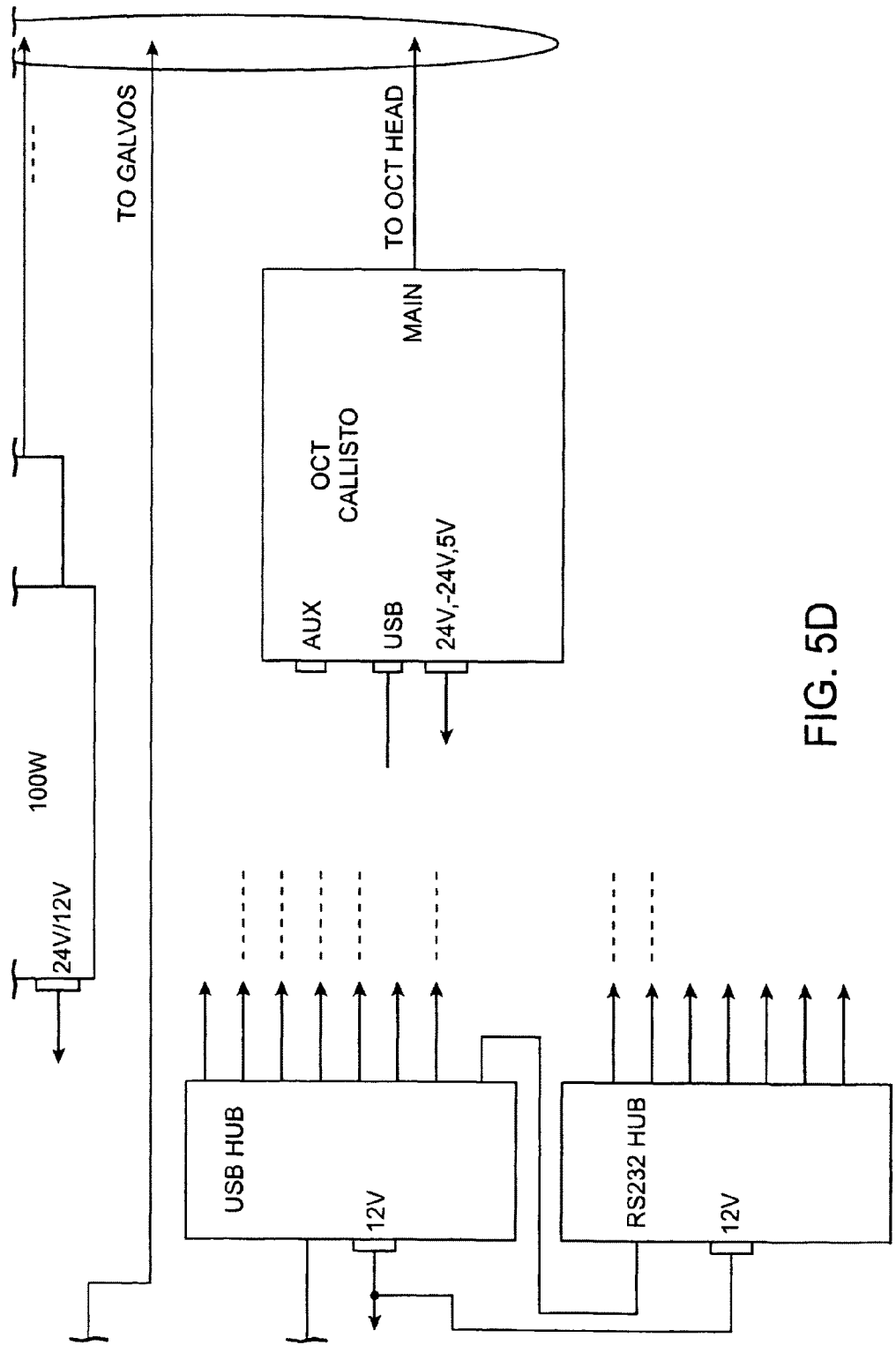
Figure 11:
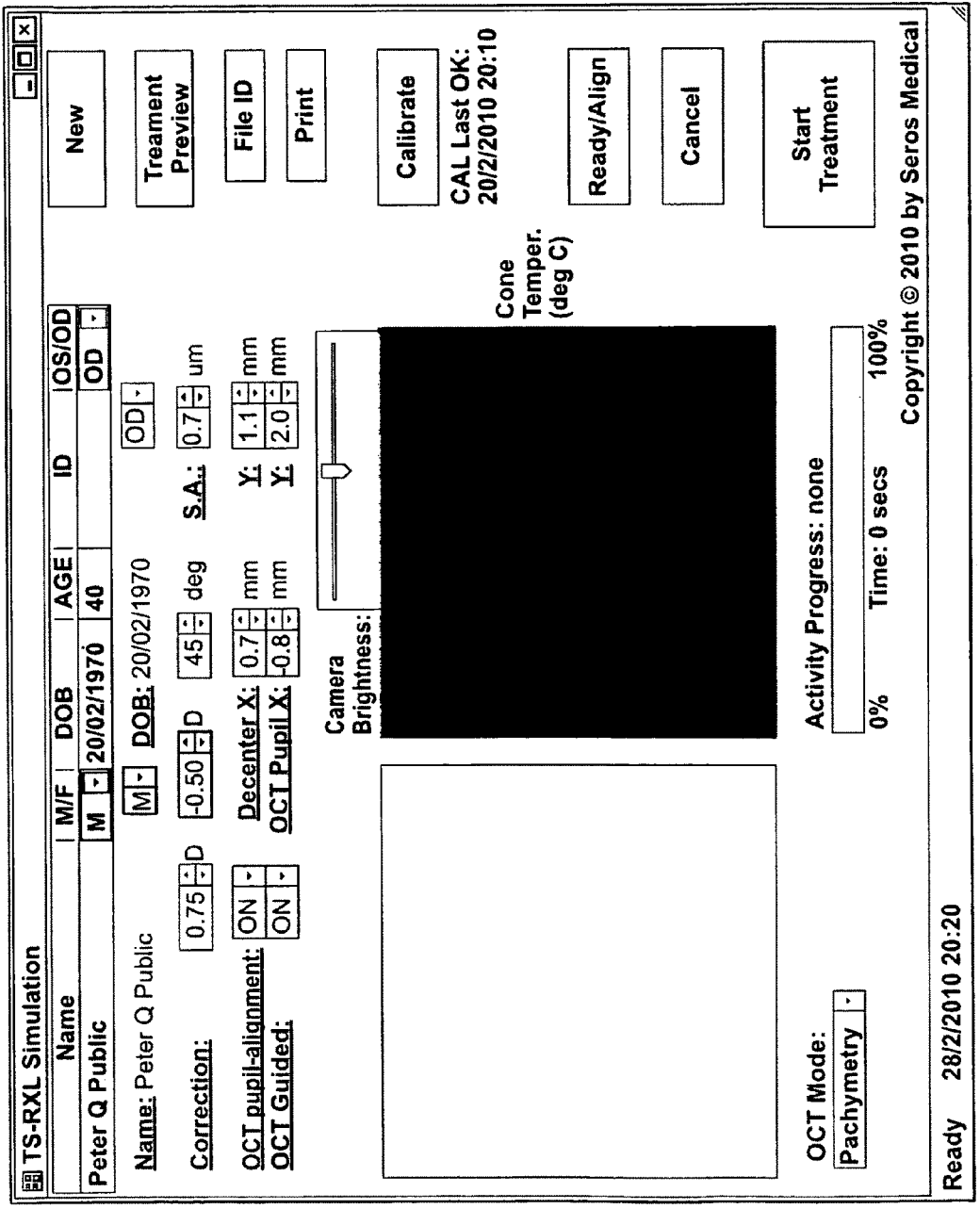
FIG. 11 is an example of the PC screen used during TS surgical setup and treatment.

The TS exemplar apparatus includes a removable and sterilizable cone assembly. FIG. 7 illustrates the components of the cone assembly. The following features are illustrated in FIG. 7: 1) sapphire lens; 2) water channel for controlling/setting the temperature of sapphire lens; 3) eye vacuum suction ring; 4) sapphire lens defogger; 5) eye illuminator; 6) eye load/force sensor. The sapphire lens is designed in a preferred meniscus shape (similar to a contact lens, see FIG. 13) and performs several functions: it is applanated to the cornea and thereby serves as a temperature control for the eye's surface, while efficiently transmitting 2.01 micron laser radiation. In addition, the sapphire lens transmits 930 nm OCT radiation, as well as visible radiation. The water channel serves as a heat-exchanger to provide programmable (i.e. presettable) temperatures (between 1 to 40 degrees C.) for the sapphire lens during thermal treatment. The eye suction ring holds the eye in place during the three treatment phases: (a) corneal pre-set treatment temperature stabilization for about 30 seconds; (b) corneal thermal control during laser thermal delivery for about 60 seconds or less; and, (c) corneal post-cooling for about 15 seconds. The suction of the ring is designed to be easily decoupled from the patient's eye by the use of about 300 mBar of vacuum. The sapphire lens defogger removes moisture from the sapphire lens surface. The illuminator delivers visible light from a fiber directly to the cone/sapphire lens in order to provide optimal camera viewing of the treatment eye during surgery, and the intensity of such light is adjustable to achieve optimal viewing. The load force sensor acts as a safety measure to alert the surgeon to any excessive pressure by the cone on the eye. The cone features are controlled as illustrated in the System Block Diagram in FIG. 5 and a typical User Interface Treatment PC screen showing control buttons is seen in FIG. 11.

Key Functions of the TS Optical System

The exemplary embodiment's optical system has four basic functions (refer to FIG. 6 and FIG. 8). The first function is the inclusion of an XY scanner that has the capability of depositing the thermal radiation into specific regions of the ocular tissue. This controlled energy deposition enables the user of the apparatus to generate a thermal profile in the ocular tissue (that has been targeted for treatment) at a desired depth, temperature range and duration. A key aspect of this thermal radiation (i.e., controlled heat transfer) is that it significantly minimizes any disruption of the epithelium and Bowman's membranes or the endothelium or conjunctiva (where the opacification due to thermal denaturation is visible in those structural and barrier protective layers). (See FIG. 8 showing the embodiment of the XY Scanner as part of the Optics System) The XY scanner is capable of a suitably small "pixel" size in delivering thermal radiation to the tissue surface, preferably in a region of between 200 μm and 1 mm in diameter, and more preferably about 600 μm in diameter. Furthermore, in the preferred embodiment, the XY scanner is capable of sweeping this region across the tissue at speeds of between 0.1 and 10 mm per second, and generally sweeps in circular regions ranging between 2 and 20 mm diameter (see FIG. 10 for examples of circular and non-circular patterns). Such parameters will be adjusted based on the energy output of the thermal radiation source in order to customize the treatment. The exemplar thermal radiation source is a CW infrared fiber laser (at approximately 2013 nm) delivering energy between 500 mW and 2 Watts. Adjustment of the power output, XY sweep speed, path pattern and pixel diameter will impact the energy delivered in a given tissue surface area.

The second function of the TS optical system is the delivery of CW infrared laser radiation to the cornea to make refractive corrections to its surface. A fundamental advantage of the inventive TS thermal delivery over other thermal delivery systems (those mentioned above) is the use of a rapid scanning laser beam (commonly referred to as "flying spot") (created by a scanner, such as the XY scanner) that enables the automatic creation of continuous patterns at optimized stable fluence rates. Previous thermal delivery systems have only used a series of cone-like treatment spots. However, continuous patterns placed in the cornea (stromal area) by the TS System result in more evenly distributed and smoother changes of local corneal curvatures, and thereby produce improved visual acuity. Moreover, the TS optical system permits the selection and adjustment of a variety of treatment parameters, including: 1) the size and position of the laser focus; 2) the shape (circular or elliptical) and dimension of the radiation patterns; 3) the speed at which the laser spot moves; and, 4) the control of duty cycles for the formation of astigmatism correction patterns.

The third function of the TS optical system is to provide the requisite safety for the TS thermal procedure. The safety system includes an iris and pupil imaging camera to ensure the cornea is in the correctly centered position when the suction ring is applied to the cornea surface. Failure to achieve accurate centering of the suction ring on the pupil could cause unpredictable and sight threatening adverse outcomes. An infrared camera is used to determine the center of the pupil, and the desired treatment pattern is then automatically aligned with respect to the patient pupil center. This process is followed by an aiming beam which locates or positions the treatment pattern over the corneal surface area to be reshaped. This area is displayed on a monitor to permit inspection and evaluation by the surgeon.

The fourth function of the TS optical system is the use of optical coherence tomography (OCT) during the thermal irradiation. This OCT application provides an accurate picture in RT of the progress of the treatment and permits immediate adjustments by the surgeon based on the RT information if necessary or desired. Furthermore, the scan positions and laser power can be constantly monitored in RT by the OCT. In the event of deviations from a programmed nomogram or laser failure, the laser can be manually or automatically or manually switched off (e.g., one millisecond) by a mechanical shutter. In addition, an aiming beam enables the TS thermal procedure to be video recorded.

Optical and Thermal System Modelling

Figure 12:
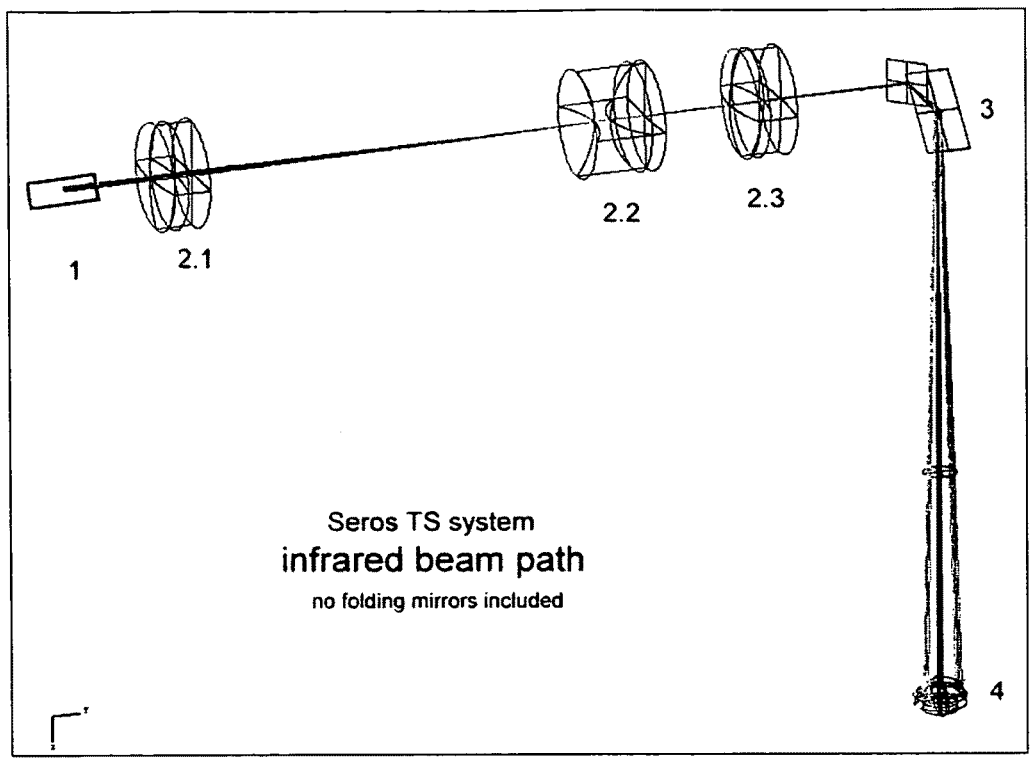
FIG. 12 shows the thermal laser beam path in the system CAD model

Optical modelling (using ZEMAX software) was used on an embodiment of the invention to ensure that the thermal laser beam which reaches ocular tissue has all the characteristics necessary to provide a successful treatment (thermal re-modelling). The Model demonstrated that a laser beam, which has an adjustable size, can reach ocular tissue at predetermined locations to generate desired patterns (without sacrificing uniformity or quality) for different types of refractive corrections. FIG. 12 models the important optical components that control the thermal laser beam size and position. This beam leaves the fiber collimator (Label 1) with a diameter of 1.2 mm. A three-lens telescope (Labels 2.1 to 2.3) reduces the magnification of the beam and focuses the treatment spot onto an applanating lens (Label 4) in front of the ocular tissue. The spot size can be adjusted by shifting the middle lens (Label 2.2) along the optical axis.

Once the range of spot diameters has been evaluated, the Model analyses the beam path that travels through the telescope and the XY-scanner. The scanner has metal surface mirrors (Label 3) which are utilized to direct the beam to the correct locations on the ocular tissue. These minors can move rapidly (up to 1 kHz) to generate circular, elliptic, or oval patterns in a continuous fashion. The central beam path in FIG. 12 shows the neutral position of the scanning mirrors. Importantly, this position is only shown for modelling purposes and is not intended to be used in an actual treatment. This also applies to the central spots in FIG. 13 and FIG. 14

FIG. 13 shows modelling of the thermal laser beam entering into the ocular tissue at different scan positions. Before the beams reach the ocular tissue they travel through a sapphire lens in contact with eye. Due to the special meniscus shape (a steep outer curvature) of this lens, the beams enter the ocular tissue at approximately a 90° angle. This angle of entry provides uniform distribution of the heat in the tissue, which results in more stable and predictable coagulation patterns. It should be noted that the beams in the model depict penetration through the ocular tissue. This is shown for modelling purposes and does not occur. Unlike the actual absorption of laser energy into ocular tissue, in FIG. 13 the Model depicts ray traces through the ocular tissue. However, in actual treatment, the penetration depth of the thermal laser beam only extends 200 μm-500 μm into the ocular tissue.

Figure 14:
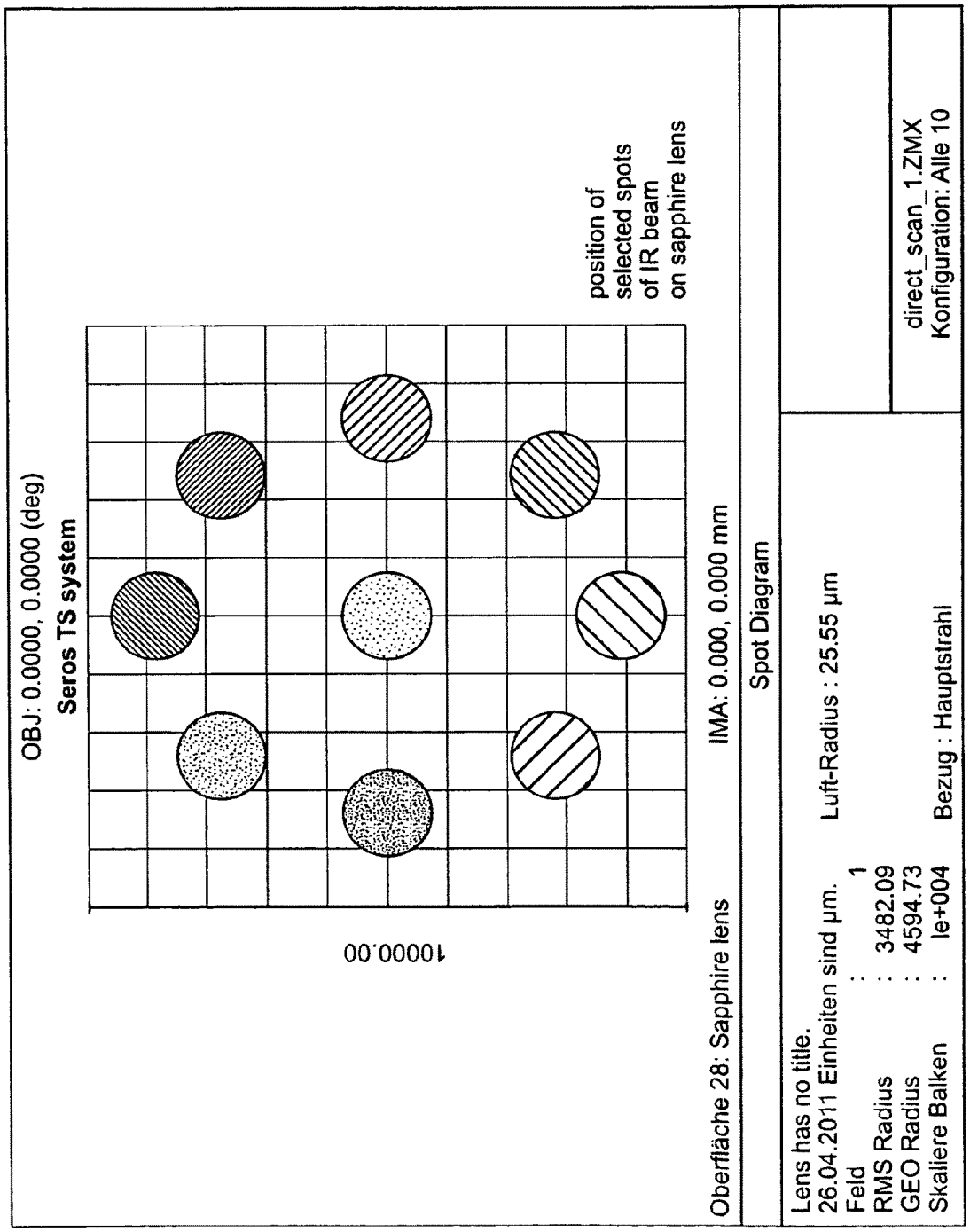
FIG. 14 shows simulated positions of selected spots on sapphire lens.

The computer controlled XY-scanner in the TS System can quickly direct the thermal laser beam to any position on the ocular tissue. FIG. 14 shows 8 spot locations at the periphery of the ocular tissue for modelling purposes. This modelling demonstrates the capability of this embodiment to deliver a range of treatment diameters and beam quality characteristics for implementation of all patterns required for the various ocular conditions mentioned herein.

Figure 15:
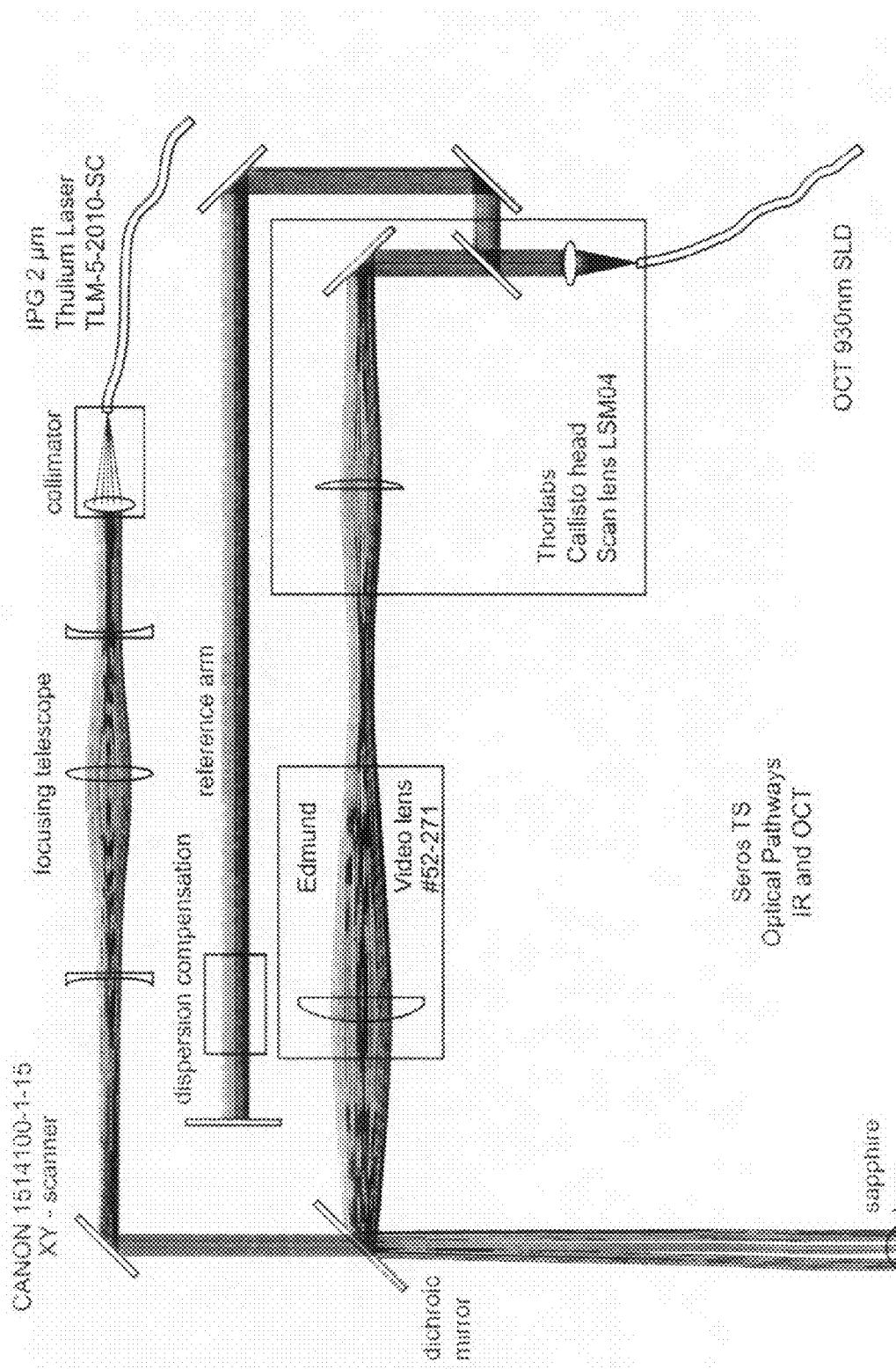
FIG. 15 shows simulated OCT beam path collinear with the thermal laser through the XY scanner to the sapphire lens.

Another novel feature of the TS system is the incorporation of an independent optical coherence tomography (OCT) imaging system that works co-axially with the thermal treatment beam (see FIG. 15). Presently, OCT contains a remote scanning capability that provides high resolution. The lateral resolution is comparable to that of a standard microscope in the order of 10 to 15 μm. The OCT system uses a wavelength in the near infrared range ($\lambda$=930 nm) which allows for the desired penetration (in the millimetre range) into biological tissue. All these features make the OCT a preferred method to on-line visual observations of the progress of the photocoagulation of a particular pattern in a TS treatment. Regions in which photocoagulation has already occurred show up clearly as light gray areas in an OCT image.

A dichroic mirror that is highly transparent for the thermal infrared radiation and also highly reflective for the OCT light is utilized, as shown in FIG. 15, which enables the combination of two different wavelengths. Thus, this type of mirror permits co-axial operation of both the treatment and the observation tasks. Referring to FIG. 15, the OCT light is directed through the Edmunds Video lens at the dichroic mirror and reflected 90 degrees by the mirror. The thermal radiation is directed at the dichroic mirror at a 90 degree angle to incoming OCT light and passes through the mirror, with no change in angle. The OCT light that is reflected and thermal radiation that passes through the mirror are coaxial, thus having a common axis. The OCT light, is concentric to or around the thermal radiation as each pass through the sapphire lens. In this way, deformation free OCT imaging is ensured. Otherwise, without the coaxial emission, the OCT can present a distorted view if it uses an independent path, such as at an angle onto the treatment locations different from that of the thermal radiation. One embodiment could include a single XY scanner and dichroic mirror appropriately located for both coaxial OCT and CW fiber laser with simultaneous scanning, but not independent scanning. The OCT images can be used for both the qualitative examination of the treatment's progress by the surgeon, and also for quantitative 3D-measurements in the micrometer range.

Embodiments of the invention include a method for treatment of ocular tissue comprising treating ocular tissue with thermal radiation and obtaining measurements from a measurement system to monitor the effect of the thermal radiation on the ocular tissue, the measurement system selected from the group consisting of fluorescent monitoring, topographic measurement, and optical coherence tomography (OCT). The method further includes adjusting parameters of the thermal radiation treatment based on the measurements. The parameters may be radiation dose, temperature of the ocular tissue, intensity of the radiation, duration of the radiation, or a pattern of exposure radiation on the ocular tissue. As discussed above, target temperatures in the various layers and the thermal remodeling outcome targets are a function of several variables or parameters which are interdependent or coupled: laser wavelength, laser power, laser scan speed, laser beam spot diameter, and sapphire temperature. Various exemplary ranges of these variables include:

laser wavelength: 1.8 μm to 6 μm;
laser power: 2 Watts (at 2.01 um) or less;
laser scan speed: 10 mm/sec or less;
laser beam spot diameter: 200 um to 1 mm;
sapphire temperature: 1 degree C. to 40 degrees C., 8 deg C. to 18 deg C.

The invention can include any combination of these ranges of the various variables.

Exemplary target temperatures can include:

a) tissue at a depth from the sapphire lens to at least 100 μm heated to no more than approximately 50 degrees C. during treatment, b) no more than approximately 75 degrees C. of peak temperature rise in a sub-surface volume in the stromal induced in a time period of under 60 seconds when sequentially irradiating 3 mm, 4 mm, and 5 mm diameter annuli, and c) lesion volume adjustable to a fine (less than approximately 50 μm×50 μm) precision for +/−0.5 Diopters control.

Additionally, safety constraints can include: i) irradiation does not heat tissue to over 75 degrees C. at any depth from sapphire lens, and ii) the lesion width in the direction perpendicular to scan motion is adequate for multiple rings (contiguous, if desired, for reduced High Order Aberrations, or discrete, if desired, for multi-focality).

The influence on the various parameters was studied with three-dimensional thermal modeling techniques. The thermal modeling was performed with human eye parameters using various combinations of the parameters discussed above with a 2.01 μm laser wavelength with a penetration depth of 0.5 mm.

EXAMPLE 1

Parameters: laser beam scan speed was at 0.4 mm/sec, thermal power at 500 mW, spot diameter at 0.5 mm, sapphire at 8 degrees C.

Outcomes:
lesion center peak temperature at 200 μm depth from sapphire is at 62 degrees C. steady state;
lesion peak temperature at 100 μm from sapphire is 51 degrees C.;
lesion width in direction of motion is at 45 μm and 30 μm perpendicular to direction of motion; and
volumetric heating of over 50 degrees C. occurs for 110 msecs.

EXAMPLE 2

Parameters: laser beam scan speed at 0.5 mm/sec, thermal power at 500 mW, spot diameter at 0.5 mm, sapphire at 8 degrees C.

Outcomes:
lesion center peak temperature at 200 μm depth from sapphire is at 55 degrees C. steady state;
lesion peak temperature at 100 μm from sapphire is 47 degrees C.;
lesion width in direction of motion is at 45 μm and 25 μm perpendicular to direction of motion; and
volumetric heating of over 50 degrees C. occurs for 50 msecs.

EXAMPLE 3

A faster moving laser beam was used to shorten the treatment time. In order to raise the temperature without increasing the laser power the sapphire temperature was increased to 18 degrees C.

Parameters: laser beam scan speed at 0.7 mm/sec, thermal power at 500 mW, spot diameter at 0.5 mm, sapphire at 18 degrees C.

Outcomes:
lesion center peak temperature at 200 μm depth from sapphire is at 55 degrees C. steady state;
lesion peak temperature at 100 μm from sapphire is 51 degrees C.;
lesion width in direction of motion is at 45 μm and 30 μm perpendicular to direction of motion; and
volumetric heating of over 50 degrees C. occurs for 50 msecs.

EXAMPLE 4

The effect of a bigger beam diameter is examined. The beam diameter is increased to 0.7 mm. The irradiance remains constant, so the beam power becomes 1000 mW.

Parameters: laser beam scan speed at 0.7 mm/sec, thermal power at 1000 mW, spot diameter at 0.7 mm, sapphire at 8 degrees C.

Outcomes:
lesion center peak temperature at 200 μm depth from sapphire is at 60 degrees C. steady state;
lesion peak temperature at 100 μm from sapphire is 50 degrees C.;
lesion width in direction of motion is at 75 μm and 40 μm perpendicular to direction of motion;
volumetric heating of over 50 degrees C. occurs for 100 msecs.

EXAMPLE 5

The effect of the bigger beam diameter and an even faster scan rate are analyzed. To compensate for the reduced volumetric heating, the sapphire temperature is raised to 18 degrees C.

Parameters: laser beam scan speed at 1 mm/sec, thermal power at 1000 mW, spot diameter at 0.7 mm, sapphire at 18 degrees C.

Outcomes:
lesion center peak temperature at 200 μm depth from sapphire is at 60 degrees C. steady state;
lesion peak temperature at 100 μm from sapphire is 50 degrees C.;
lesion width in direction of motion is at 75 μm and 40 μm perpendicular to direction of motion;
volumetric heating of over 50 degrees C. occurs for 100 msecs.

The scan speed of 1 mm/sec permits the 3 mm, 4 mm, and 5 mm diameter rings to be sequentially delivered in a total treatment time of about 40 seconds. At temperatures between 50 degrees C. and 70 degrees C., collagen takes about 10 seconds to 60 seconds to shrink to the maximum extent (to 30% of its original length—linear phase I). A starting volume of collagen stromal tissue ranging from about 45 μm×25 μm×200 μm up to about 75 μm×40 μm×300 μm linearly can be selectably shrunk for a period of time up to about 10 second duration in any pattern (annular for example, diameter selectable) sub-surface (depth selectable for example within the stroma). This is accomplished while meeting all the aforementioned safety criteria (including for example the ability of an intra-operative OCT to detect the appearance of lesions of such dimensions.

Photochemical Cross-Linking Therapeutic Modality

In addition to the thermal radiation delivery (set forth above) for reshaping ocular tissue, the invention herein includes the application of cross-linking corneal tissue before, during, after, or any combination thereof of the above described thermal radiation procedure. Such cross-linking could be performed at any time within six months prior to the thermal procedure or at any time six months after the thermal procedure. The key feature of the invention is that there is a combination of thermal treatment together with cross-linking in order to obtain successful results from this invention. It is known in the literature that thermal reshaping of corneal collagen tissue will regress to nearly its original state. However, the invention herein contemplates that if cross-linking of such collagen tissue is performed, the rate of regression will be significantly reduced or eliminated. Cross-linking can provide stability/rigidity collagen tissue for a period of many years. Although it has not been clinically tested, it is believed that the combination of thermal radiation reshaping (TS), together with cross-linking, can provide a successful treatment for the diseases and conditions mentioned hereinabove. According to the invention, photochemical (such as riboflavin-UVA) minimally-invasive cross-linking of ocular collagen tissue is provided for the purpose of securing stability (i.e., to maintain stiffness/rigidity) and preventing or slowing regression of the treated tissue over an extended period of time, and preferably for a period of two to twenty years.

Tissue-Sparing Rapid Cross-Linking (TS-RXL) Process

The rapid cross-linking (RXL) technologies of the invention address the disadvantages of the current cross-linking procedures (CXL). Some of the RXL technologies that may be deployed as part of the invention include: 1) enhanced riboflavin formulations (including those with deuterated water and/or pharmacological penetration enhancers), described in WO 2011/019940; 2) photosensitizer (riboflavin) epithelium-sparing delivery into the corneal stroma with the use of micro-needle arrays (MNA) (as described in U.S. Patent Application No. 61/443,191, which is incorporated by reference herein) or using Laser Induced Stress Waves (LISW); 3) UVA delivery mats in the shape of a contact lens that fit under the eye lid, as described in U.S. Patent Application No. 61/443,191; 4) UVA energy patterns using pulsation and fractionation; 5) the creation of an oxygen-enriched ambient environment (such as an eye mask or oxygen dispensing tube) for ocular tissue in-gassing.

Some or all of the aforementioned technologies may be employed to achieve the key benefits of the RXL process, which are:

1) Non-invasiveness; RXL procedures do not require removal and/or debridement of the corneal epithelium, reducing intra-operative or post-operative pain and delayed visual recovery;

2) Speed; RXL procedure can be under 15 minutes for two eyes vs. approximately 1 hour per eye for CXL;

3) Precision; RXL according to the invention provides more precise treatments due to: (a) better patient alignment to the UVA; (b) precisely timed automated riboflavin delivery with penetration feedback;

4) Uniformity; The RXL beam profile (temporal and spatial) of UVA is uniform, as opposed to the CXL Gaussian beam profile. The former achieves more accurate and reproducible uniform cross-linking results.

5) Increased Energy Output. There is flexibility in RXL to increase the UVA intensity from 9-100 mWcm$^2$ compared with the basic fixed CXL intensity of 3 mWcm$^2$. Using increased intensity enables the patient's treatment time to be dramatically reduced.

6) Increased Energy Tailoring. Because of the higher UVA irradiance, the RXL beam can be pulsated and fractionated, which enables the cross-linking to take effect more efficiently.

7) Scleral Delivery. RXL can be configured for scleral delivery (see FIG. 10).

Riboflavin Pre-Soak Preparation for RXL

As previously noted, in the current CXL process, it is normal to pre-soak corneal tissue through the use of riboflavin eye drops (every 3 minutes) for 30 minutes (per eye) prior to UVA irradiation. However, the inventive RXL process greatly reduces the pre-soak time. The RXL invention contemplates the use of MNA or LISW to quickly (within 2 to 15 minutes) deliver riboflavin into the corneal stroma that is sufficient for crosslinking.

Enhanced Riboflavin Formulations

RXL requires the necessary absorption and activation of riboflavin in the stroma. In order to achieve these absorption and activation conditions, novel riboflavin formulations are used in RXL (the same as mentioned above in the description of fluorescence monitoring of temperature). This formulation may contain pharmacological penetration enhancers such as benzalkonium chloride (BAC), and oxygen radical lifetime enhancers such as deuterated water ($D_2O$). An unexpected benefit of the combination of RXL and thermal radiation is that deuterated solutions serve as greater thermal barriers for the tissue surface than conventional solutions.

Stromal Oxygen Enrichment

During the cross-linking UVA delivery phase, dissolved oxygen is consumed by the creation of reactive oxygen species (ROS). It is the ROS that activates cross-linking (i.e., Type II photo-sensitizer reaction). Thus, the dissolved oxygen is critical in order to produce the molecular reaction in the collagen tissue that results in covalent bonding. If the dissolved oxygen is not present, the process shuts down. Significantly, the deuterated riboflavin formulation has a novel capability that permits pre-loading of a high concentration of dissolved oxygen. This capability guarantees that the ROS process will proceed unabated.

The foregoing is not meant to limit the invention, as it should be noted that there are other means to diffuse oxygen gas into the stroma, which might include, among others, the use of a device that would deliver such oxygen gas to the corneal surface. This oxygen gas then diffuses (albeit slowly) into the stroma, thereby increasing dissolved oxygen.

In summary, the ability to increase dissolved oxygen in the stroma enables the use of a higher UVA irradiance exposure to the collagen tissue. In turn, this means that optimum cross-linking can be achieved in a shorter period of time.

UVA Fractionation and Pulsation

The application of UVA irradiation to riboflavin surrounding collagen in the corneal stroma induces hypoxia (at rates proportional to the intensity of UVA irradiation). Excessive hypoxia (which can be caused by a long period of UVA irradiation) can result in endothelial and keracocyte cytotoxicity, and such excess does not enhance cross-linking of collagen tissue. One of the only direct means to prevent hypoxia is to permit ambient (or ancillary bottled) oxygen to diffuse into the stroma, however, this is a slow process. Treatment of 30 seconds to 2 minutes is required for ambient oxygen to diffuse and traverse throughout the stroma.

In order to provide a more efficient system for optimizing the effect of cross-linking (i.e., perform cross-linking in the cornea more rapidly), and, at the same time prevent excessive apoptosis, the apparatus of the invention has the ability to employ a photo dynamic therapy (PDT) technique herein called fractionation (where the UVA irradiation is turned on and off at pre-selected intervals, e.g., 30 seconds). When this technique is applied in the presence of deuterated water or $D_2O$ (one of the novel ingredients in the riboflavin formulation) up to a ten-fold increase in cross-linking density can be achieved without inducing significant hypoxia. Significantly, the RXL process is able to create Type II photo-sensitizer reactions in its collagen cross-linking pathway and thereby generate singlet reactive oxygen species (ROS).

It is inefficient to continuously irradiate with UVA during the cross-linking procedure. In effect, by so doing the dissolved oxygen becomes depleted with no recovery. The concentration of ROS generated in the stroma is linearly correlated to the UVA irradiation (all else being equal). Therefore, the apparatus employs a pulsation technique whereby 50 micro-second pulsations are utilized to maintain the amount of ROS the RXL System has generated. This allows the system to function with less total UVA dosage than used by the typical cross-linking application. Thus, the pulsation and fractionation employed by the RXL System can be synchronized to make cross-linking far more efficient (e.g., exposure time, crosslink density, and preventing kerato/endo apoptosis) and more effective than CXL.

Figure 9:
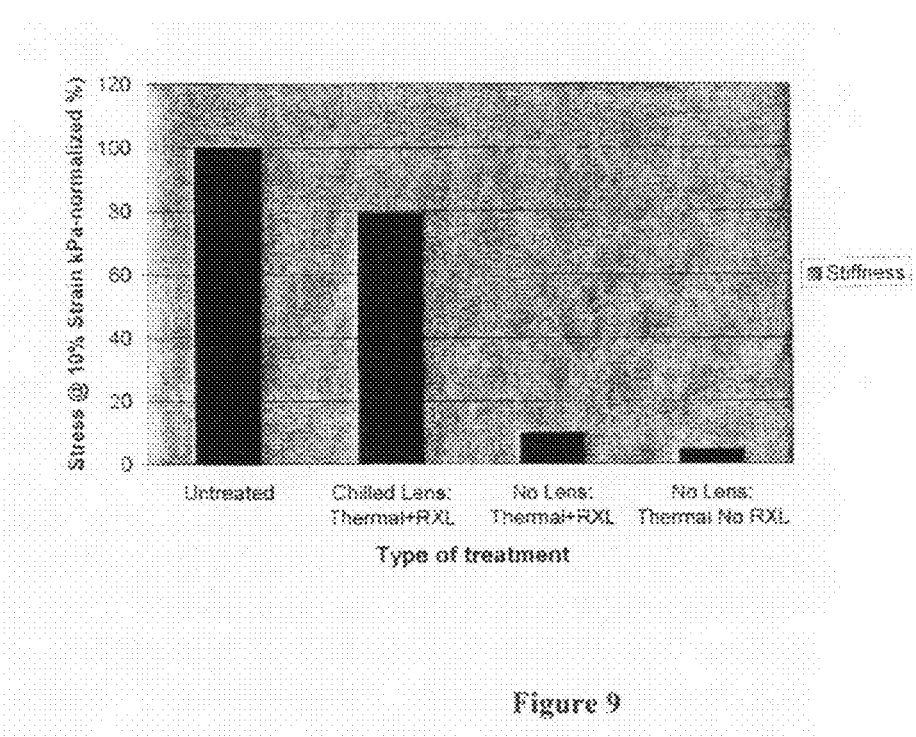
FIG. 9 is a chart that illustrates the comparison of corneal stiffness achieved from cross-linking with and without the use of a chilled lens at the time of thermal delivery.

Experimental Evidence Demonstrating Benefit of RXL Following Sub-Surface Thermal Control/Cooling The chart in FIG. 9 shows the stability (stiffness) of porcine ocular tissue following thermal delivery in vitro. It demonstrates the value of the surface thermal control/cooling, using a custom applanation lens as a thermal control/cooling device, as it prevents damage to the epithelium and Bowman's membranes which may be caused by thermal lesions. Stability is significantly less in a cross-linked cornea where the epithelium and Bowman's layers have been damaged by the thermal radiation application, as in prior art methods. However, when a thermal control/cooling technique is used during the thermal treatment according to the present invention, such as the TS sapphire lens, and then RXL cross-linking is performed, tests show that up to 80% stiffness can be retained in the ocular tissue. Whereas, if there is no surface thermal control/cooling with thermal delivery, the cross-linking of the stiffness factor rises to no more than 10%.

Typical Procedural Steps

The following description represents one possible procedure for implementing the present invention. It assumes patient informed consent has been obtained and the instrument has been calibrated, the patient eye or eyes to be treated have been specified and the treatment plan or template has been specified. The present invention is not limited to this procedure and variations from the procedure are within the scope of the invention.

Pre-Op Preparation:

Instill topical anesthetic: proparacaine or tetracaine. Wait 5 minutes before proceeding to pre-soak.

Riboflavin pre-soak: Using micro-needle arrays or laser induced stress waves (LISW), riboflavin formulation is delivered intra-stromally.

Five minutes of soak time is allotted thereafter for proper diffusion.

UVA step: A calibrated contact lens mat is inserted into each eye and the 10 minute count down timer started on the PC screen. The patient eye lids can be closed or partially closed.

TS Surgical Procedure

Instill topical anesthetic: proparacaine or tetracaine. Wait 5 minutes before proceeding to alignment and coupling step. Set the XYZ adjustable treatment cone in the "Home" position and Cone lens temperature to 8 deg C.

Patch Contra-Lateral Eye

Alignment and Coupling:

(1) Patient supine at TS System bed, insert eyelid speculum.

(2) Adjust bed height so that treatment eye is less than 1 cm from cone; help in visualization is provided by the 2 live video cameras on the PC screen.

(3) Adjust the cone position by the XYZ controls in order to center over patient pupil; the pupil center will be displayed on the PC screen to enable the surgeon to select the treatment center.

(4) Turn ON suction ring to lock the eye in place.

Thermal Delivery:

(1) System forces wait of 30 seconds after applanation to permit cornea to cool (2) Preview treatment pattern/alignment on the PC display screen (3) Confirm step #2 by pressing the "Ready to Treat" on the touch screen display (4) Press footswitch to start and continue pressing until end of treatment (approximately 60 seconds)

(5) The System forces a wait of 15 seconds after step #4 completed for cool down (6) The System automatically shuts off vacuum on the suction ring after cool down Treat contra-lateral eye: instill artificial tears, patch treated eye, mark, align, couple and treat contra-lateral eye as described above.

Bilateral Simultaneous Same Day Cross-linking (RXL)

UVA Treatment:

(1) The patient remains supine on TS-RXL bed, (2) Instill one drop of topical anesthetic in both eyes (3). Insert UVA cones in the treatment arm of the TS-RXL System (4) Align and applanate UVA cones to the respective corneal centers using standby UVA illumination (5) Confirm alignment and applanation with visual camera feedback on the PC display screen (6) Begin RF delivery by starting pumps (7) Start UVA exposure for 10 minutes (8) System automatically switches off UVA Exit instructions with take-home pack that includes disposable sunglasses and artificial tears.

In summary, the invention encompasses a combination of modalities that jointly enable treatment of ocular tissue for the purpose of reshaping such tissue and stabilizing (i.e., preventing regression) of the shape changes. Generally, this combination includes the use of thermal radiation, such as a CW infrared fiber laser, to treat ocular tissue with lesions that can very precisely alter the shape of the tissue in which they are placed. Additionally, this combination includes the application of cross-linking the collagen tissue in the areas surrounding the lesions. There are many novel aspects of these combined modalities. The thermal treatment uses techniques that, among others, include the following: 1) a surface thermal control/cooling system, such as a sapphire lens, that permits thermal radiation to be transferred into the tissue at a subsurface level, thereby sparing the structurally vital surface layers of the tissue; 2) the capability of placing the lesion at a pre-determined depth and with a customized adaptive pattern; 3) the ability to adjust and control tissue temperatures in order to induce uniform shrinkage from the pattern application inside ocular tissue; 4) the use of a real-time OCT-guided procedure to provide accuracy and uniformity of outcomes.

The cross-linking application for these combined modalities employs techniques that, among others, include the following: 1) the use of micro-needle arrays and/or laser induced stress waves (LISW) to rapidly instill a photochemical cross-linking agent (riboflavin) into ocular tissue without disrupting the outer layer (such as the epithelium) of the targeted tissue; 2) the use of other agents (such as $D_2O$) with riboflavin to increase the speed and uniformity of application; 3) the process of UVA activation through the use of pulsation and fractionation techniques; 4) the ability to deliver UVA through a contact lens shaped, fiber-coupled plastic mat.

It is important to note the flexibility within and between the applications of the aforementioned combined modalities. Such flexibility includes procedures whereby cross-linking can be performed either prior or subsequent to the thermal application without loss of efficacy in the procedures. It is anticipated that invention herein described will be useful to treat refractive diseases or conditions, for example myopia or glaucoma.

In the Thermal Lesion Depth Thermal Control/Cooling aspect, the tissue surface temperature and Thermal Radiation therapeutic modality are maintained at an effective level so that thermal lesions in the stroma are at a depth preserving the epithelium and Bowman's membrane. The minimum depth of the lesion is preferably approximately 80 to 100 µm below the external surface of the epithelium. Generally, the lesion may span between 100 µm and 400 µm below the external surface of the epithelium. The tissue surface temperature should be maintained at between 1 degree C. and 16 degrees C. Preferably the tissue surface temperature should be approximately 8 degrees C. The temperature may be monitored by fluorescence monitoring with an externally applied fluorophore. The lesion depth may be monitored by OCT.

In the two dimensional scanning resolution aspect, Thermal Radiation therapeutic modality XY scanner may employ a laser beam diameter at the tissue surface of between 200 µm and 1 mm, where the preferred beam diameter is approximately 600 µm.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An apparatus for treatment of ocular tissue comprising:
   a laser operative at a wavelength selected from the ranges of 1.4 µm to 1.54 µm or 1.8 µm to 6.0 µm for irradiating an ocular surface and inducing symmetrically uniform lesions in a subsurface region below the ocular surface to modify the shape of the ocular surface;
   an ocular surface cooling mechanism configured for controlling temperature of the ocular surface irradiated by the laser; and
   an ultraviolet radiation source configured to irradiate the ocular surface and the subsurface region to induce crosslinking of ocular tissue below the ocular surface in or near the lesions.

2. The apparatus of claim 1, further comprising a solution source for delivery below the surface of the ocular surface, wherein the solution promotes crosslinking of ocular tissue.

3. The apparatus of claim 2, wherein the solution is deuterated water riboflavin solution.

4. The apparatus of claim 1, wherein the laser is a continuous wave infrared fiber laser.

5. The apparatus of claim 1, wherein the cooling mechanism comprises a sapphire lens configured to applanate on the ocular surface.

6. The apparatus of claim 1, wherein the cooling mechanism comprises a lens made of a highly thermally conductive material configured to applanate on the ocular surface.

7. The apparatus of claim 1, wherein the cooling mechanism comprises a water channel to transport cooled water for controlling a temperature of a lens configured to applanate on the ocular surface.

8. The apparatus of claim 1, wherein the ocular surface is a cornea surface and the subsurface region comprises the stroma.

9. The apparatus of claim 1, wherein the laser wavelength selected from the range of 1.4 µm to 1.54 µm.

10. The apparatus of claim 1, wherein the laser wavelength is selected from the range of from 1.86 µm to 2.52 µm.

* * * * *